United States Patent
Bade et al.

(10) Patent No.: US 12,327,343 B1
(45) Date of Patent: Jun. 10, 2025

(54) SYSTEMS AND METHODS FOR STANDARDIZATION OF ELECTROCARDIOGRAM SIGNAL IMAGES

(71) Applicant: Anumana, Inc., Cambridge, MA (US)

(72) Inventors: Sairam Bade, Thelangana (IN); Rakesh Barve, Bengaluru (IN); Yash Mishra, Bangalore (IN); Ashim Prasad, Bangalore (IN); Shashi Kant, Bengaluru (IN); Mayank Sharma, Brookfield (IN); Durgaprasad Dodle, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/826,718

(22) Filed: Sep. 6, 2024

(51) Int. Cl.
  *G06T 7/00* (2017.01)
  *A61B 5/346* (2021.01)
  *G06T 5/50* (2006.01)
  *G06T 11/60* (2006.01)

(52) U.S. Cl.
  CPC ............ *G06T 7/0002* (2013.01); *A61B 5/346* (2021.01); *G06T 5/50* (2013.01); *G06T 11/60* (2013.01); *G06T 2207/20221* (2013.01); *G06T 2207/30168* (2013.01)

(58) Field of Classification Search
  CPC ..... G06N 20/00; G06T 7/0012; G06T 7/0014; G06T 2207/20084; G06T 2207/30004; G06V 10/141; G06V 40/166; G06V 30/194; G06V 10/10; G06V 10/70
  See application file for complete search history.

(56) References Cited

U.S. PATENT DOCUMENTS

| | | | |
|---|---|---|---|
| 2020/0160980 A1* | 5/2020 | Lyman | G06N 3/045 |
| 2020/0351439 A1 | 11/2020 | Yan et al. | |
| 2022/0375088 A1 | 11/2022 | Shah et al. | |
| 2023/0029070 A1 | 1/2023 | Buelow et al. | |
| 2023/0252635 A1* | 8/2023 | Hasegawa | A61B 6/54 |
| | | | 382/128 |

(Continued)

OTHER PUBLICATIONS

Wüller, Dietmar, and Ulla Bøgvad Kejser. "Standardization of image quality analysis—ISO 19264." Archiving Conference. vol. 13. Society for Imaging Science and Technology, 2016. (Year: 2016).*

(Continued)

*Primary Examiner* — Li Liu
(74) *Attorney, Agent, or Firm* — Caldwell Intellectual Property Law

(57) ABSTRACT

An apparatus for standardization of electrocardiogram signal images, the apparatus having an imaging device, at least a processor and a memory communicatively connected to the at least a processor, the memory containing instructions configuring the at least a processor to receive an overlay image from the imaging device, identify a captured fixed background image and a captured primary image within the overlay image, wherein the captured primary image includes a plurality of electrocardiogram signals, compare the captured fixed background image to one or more image quality thresholds, determine an image quality score of the primary image as a function of the captured fixed background image, and output one or more image modification datum as a function of the image quality score.

20 Claims, 9 Drawing Sheets

(56) References Cited

U.S. PATENT DOCUMENTS

2023/0281789 A1    9/2023  Sudarsky et al.
2023/0388520 A1*  11/2023  Krummen .............. G06V 30/10

OTHER PUBLICATIONS

Fortune, Julian D., et al. "Digitizing ECG image: a new method and open-source software code." Computer methods and programs in biomedicine 221 (2022): 106890. (Year: 2022).*

Shivashankara, Kshama Kodthalu, et al. "ECG-Image-Kit: a synthetic image generation toolbox to facilitate deep learning-based electrocardiogram digitization." Physiological Measurement 45.5 (2024): 055019. (Year: 2024).*

Lence, Alex, et al. "Automatic digitization of paper electrocardiograms—A systematic review." Journal of Electrocardiology 80 (2023): 125-132. (Year: 2023).*

* cited by examiner

SYSTEMS AND METHODS FOR STANDARDIZATION OF ELECTROCARDIOGRAM SIGNAL IMAGES

FIELD OF THE INVENTION

The present invention generally relates to the field of image modification. In particular, the present invention is directed to standardization of electrocardiogram signal images.

BACKGROUND

The image quality of electrocardiogram (ECG) signals on ECG strips and/other physical visualizations of electrocardiograms signals may be influenced by camera characteristics such as auto-focus, flash, resolution, and image compression. Environmental factors like document placement, camera angle, light sources, exposure time, and background colors may also impact image quality. Current systems used to determine the image quality of ECG signals are lacking and can thus alter or skew determinations made on the image.

SUMMARY OF THE DISCLOSURE

In an aspect an apparatus for standardization of electrocardiogram signal images is described. The apparatus includes an imaging device, at least a processor and a memory communicatively connected to the at least a processor. The memory containing instructions configuring the at least a processor to receive an overlay image from the imaging device, identify a captured fixed background image and a captured primary image within the overlay image, wherein the captured primary image includes a plurality of electrocardiogram signals, compare the captured fixed background image to one or more image quality thresholds, determine an image quality score of the primary image as a function of the captured fixed background image, and output one or more image modification datum as a function of the image quality score.

In another aspect, a method for standardization of electrocardiogram signal images is described. The method includes receiving, by an imaging device, an overlay image, identifying, by at least a processor, a captured fixed background image and a captured primary image within the overlay image, wherein the captured primary image includes a plurality of electrocardiogram signals, comparing, by the at least a processor, the captured fixed background image to one or more image quality thresholds, determining, by the at least a processor, an image quality score of the primary image as a function of the captured fixed background image and outputting, by the at least a processor, one or more image modification datum as a function of the image quality score.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for standardization of electrocardiogram signal images. In an aspect, the present disclosure includes an input device configured to receive overlay images and a computing device configured to determine the quality of the overlay images.

Aspects of the present disclosure can be used to determine the quality of images generated by an imaging device. Aspects of the present disclosure can further be used to modify configurable settings on imaging devices. Exemplary embodiments illustrating aspects of the present disclosure are described below in the context of several specific examples.

Figure 1:
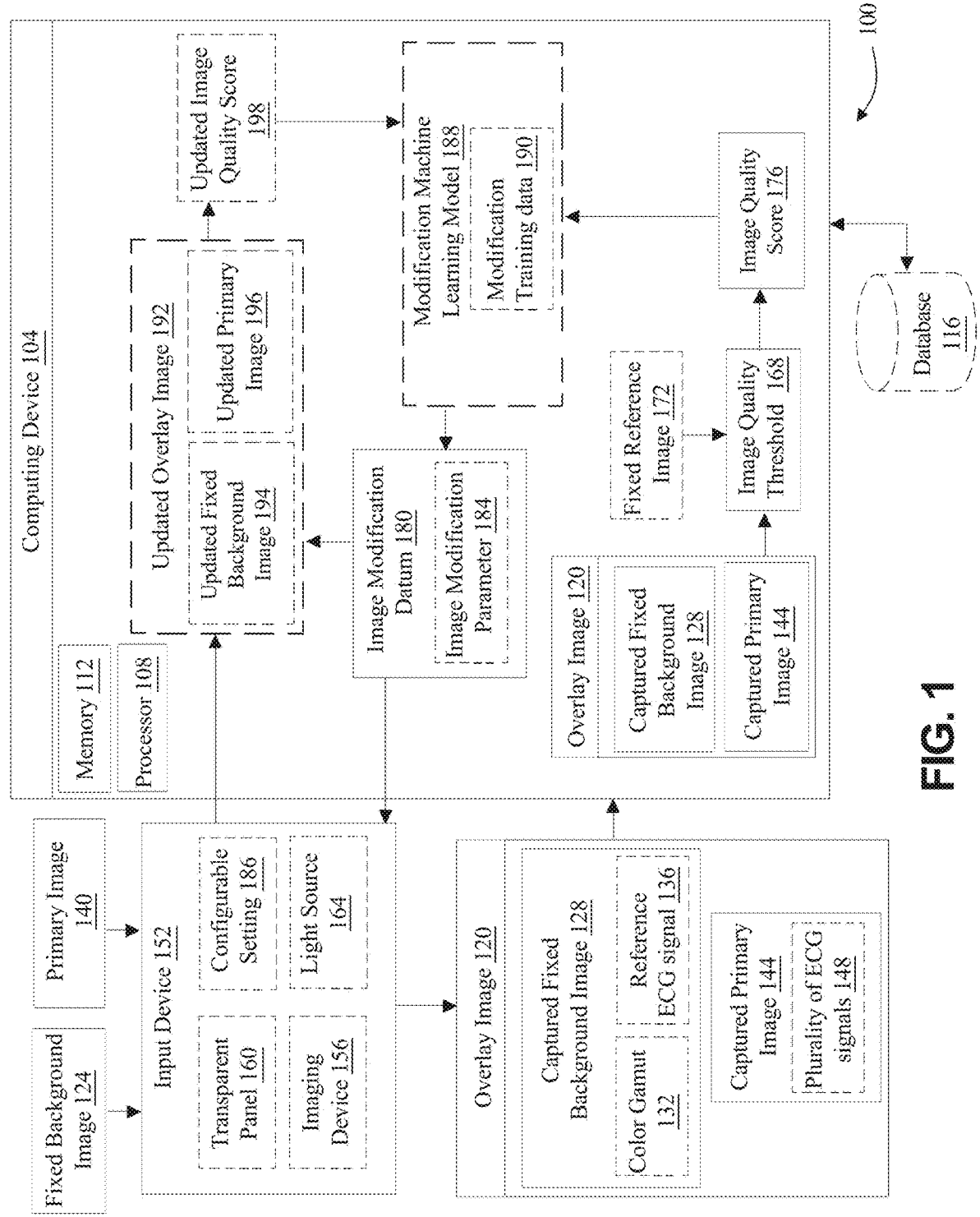
FIG. 1 is an exemplary embodiment of an apparatus for standardization of electrocardiogram signal images.

Referring now to FIG. 1, a apparatus 100 standardization of ECG signal images is described. In one or more embodiments, apparatus 100 may be configured to predict any medical condition and/or medical disease. Apparatus 100 includes a computing device 104. Apparatus 100 includes a processor 108. Processor 108 may include, without limitation, any processor 108 described in this disclosure. Processor 108 may be included in a and/or consistent with computing device 104. In one or more embodiments, processor 108 may include a multi-core processor. In one or more embodiments, multi-core processor may include multiple processor cores and/or individual processing units. "Processing unit" for the purposes of this disclosure is a device that is capable of executing instructions and performing calculations for a computing device 104. In one or more embodiments, processing units may retrieve instructions from a memory, decode the data, secure functions and transmit the functions back to the memory. In one or more embodiments, processing units may include an arithmetic logic unit (ALU) wherein the ALU is responsible for carrying out arithmetic and logical operations. This may include, addition, subtraction, multiplication, comparing two data, contrasting two data and the like. In one or more embodiments, processing unit may include a control unit wherein the control unit manages execution of instructions such that they are performed in the correct order. In none or more embodiments, processing unit may include registers wherein the registers may be used for temporary storage of data such as inputs fed into the processor and/or outputs executed by the processor. In one or more embodiments, processing unit may include cache memory wherein memory may be retrieved from cache memory for retrieval of data. In one or more embodiments, processing unit may include a clock register wherein the clock register may be configured to synchronize the processor with other computing components. In one or more embodiments, processor 108 may include more than one processing unit having at least one or more arithmetic and logic units (ALUs) with hardware components that may perform arithmetic and logic operations. Processing units may further include registers to hold operands and results, as well as potentially "reservation station" queues of registers, registers to store interim results in multi-cycle operations, and an instruction unit/control circuit (including e.g. a finite state machine and/or multiplexor) that reads op codes from program instruction register banks and/or receives those op codes and enables registers/arithmetic and logic operators to read/output values. In one or more embodiments, processing unit may include a floating-point unit (FPU) wherein the FPU may be configured to handle arithmetic operations with floating point numbers. In one or more embodiments, processor 108 may include a plurality of processing units wherein each processing unit may be configured for a particular task and/or function. In one or more embodiments, each core within multi-core processor may function independently. In one or more embodiments, each core within multi-core processor may perform functions in parallel with other cores. In one or more embodiments, multi-core processor may allow for a dedicated core for each program and/or software running on a computing system. In one or more embodiments, multiple cores may be used for a singular function and/or multiple functions. In one or more embodiments, multi-core processor may allow for a computing system to perform differing functions in parallel. In one or more embodiments, processor 108 may include a plurality of multi-core processors. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing devices operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory 112 between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a Processor module to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, apparatus 100 includes a memory 112 communicatively connected to processor 108, wherein the memory 112 contains instructions configuring processor 108 to perform any processing steps as described herein. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 112 may include a primary memory and a secondary memory. "Primary memory" also known as "random access memory" (RAM) for the purposes of this disclosure is a short-term storage device in which information is processed. In one or more embodiments, during use of computing device 104, instructions and/or information may be transmitted to primary memory wherein information may be processed. In one or more embodiments, information may only be populated within primary memory while a particular software is running. In one or more embodiments, information within primary memory is wiped and/or removed after computing device 104 has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 108 may access the information from primary memory.

Still referring to FIG. 1, apparatus 100 may include a database 116. Database may include a remote database 116. Database 116 may be implemented, without limitation, as a relational database, a key-value retrieval database such as a NOSQL database, or any other format or structure for use as database that a person skilled in the art would recognize as suitable upon review of the entirety of this disclosure. Database may alternatively or additionally be implemented using a distributed data storage protocol and/or data structure, such as a distributed hash table or the like. Database 116 may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, apparatus 100 may include and/or be communicatively connected to a server, such as but not limited to, a remote server, a cloud server, a network server and the like. In one or more embodiments. In one or more embodiments, computing device 104 may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by system computing device 104. In one or more embodiments, computing device 104 may transmit processes to server wherein computing device 104 may conserve power or energy.

With continued reference to FIG. 1, processor 108 is configured to receive an overlay image 120. An "overlay image" as used in this disclosure is an image depicting two separate physical elements that are positioned atop one another. For example, and without limitation overlay image 120 may include an image of two photographs in which a first photograph is positioned atop a second photograph. In one or more embodiments, overlay image 120 may include an image of a first element positioned atop and slightly obstructing a second element. In one or more embodiments, first element and/or second element may include physical photographs, physical printouts, physical illustrations, physical objects and the like. A "physical element" for the purposes of this disclosure refers to anything tangible. For example, and without limitation, physical element may include a physical printout of an image. In one or more embodiments, physical elements may include but are not limited to printed images, physical objects, goods and the like. In one or more embodiments, physical elements may include printouts generated by computing device 104. in one or more embodiments, physical element may include first element and second element. In one or more embodiments, overlay image 120 may include an image of two physical elements in which first element may be partially obstructing second element. In one or more embodiments, second element may be physically larger than first element wherein first element may only be capable of partially obstructing second element. In one or more embodiments, first element may be situated directly on top of second element. In one or more embodiments, an entirety of first element may obstruct a portion of second element.

With continued reference to FIG. 1, overlay image 120 and/or second element includes and/or depicts a fixed background image 124. In one or more embodiments, overlay image 120 may include an image depicting a portion of fixed background image 124 and/or a captured fixed background image 128. A "fixed background image" for the purposes of this disclosure is a physical element having a predetermined shape or pattern. For example and without limitation fixed background image 124 may include an image containing predetermined patterns, such as but not limited to, squares, grids, checked boxes and the like. A "captured fixed background image" for the purposes of this disclosure refers to a captured image of fixed background image 124. For example, and without limitation, overlay image 120 may include captured fixed background image 128 wherein overlay image 120 may include a representation of fixed background image 124 in the form of a scan or photograph. In one or more embodiments, captured fixed background image 128 may include a digital representation of fixed background image 124 as captured by input device 152. In one or more embodiments, fixed background image 124 may be made from photographic paper, plastic and/or any other material. In one or more embodiments, fixed background image 124 may be partially transparent. In one or more embodiments, fixed background image 124 may include a reflective and/or transmissive material. In one or more embodiments, fixed background image 124 may have the same predetermined shape or pattern on each iteration of the processing of apparatus 100. In one or more embodiments, overlay image 120 may differ in each iteration of the processing of apparatus 100 wherein fixed background image 124 may remain the same. In one or more embodiments, angles, color profiles and the like of fixed background image 124 may be depicted differently due to quality issues in image capture of overlay image 120. In one or more embodiments, fixed background image 124 may be used as a reference during processing of one or images by computing device 104. In one or more embodiments, fixed background image 124 may include patterns such as Siemens stars, slanted-edge charts and the like. In one or more embodiments, fixed background image 124 may be used as a reference by processor 108 and/or computing device 104 in order to determine the quality of an image. In one or more embodiments, fixed background image 124 may include an image, photograph and/or the like having a predetermined size, shape, and color profile. In one or more embodiments, fixed background image 124 may include graphical visualization such as color patches including colored squares or rectangles that represent a wide range of colors. In one or more embodiments, color patches may be used to determine the color accuracy of overlay image 120. In one or more embodiments, fixed background image 124 may include a graphical visualization of geometric shapes, such as gride circles, squares and the like wherein the geometric shapes may be used to determine the amount of warping overlay image 120 may contain. In one or more embodiments, fixed background image 124 may include text that may be used to determine the quality of overlay image 120 by determining the quality of text on fixed background image 124 within overlay image 120.

With continued reference to FIG. 1, fixed background image 124 may include a color gamut 132. A "Color gamut" for the purposes of this disclosure is a set of colors that can be used to determine if a device is capable of recreating said colors. For example, and without limitation, color gamut may include 100 differing colors wherein color gamut may be used to determine if a camera is capable of capturing the 100 differing colors. A color gamut 132 may include a range of colors that can be reproduced by a particular device or system. In one or more embodiments, placement of color gamut 132 on fixed background image 124 may aid in assessing the quality of overlay image 120. In one or more embodiments, color gamut 132 may aid in the determination of the quality of colors captured in overlay image 120. In one or more embodiments, color gamut 132 may aid in the determination of the quality of colors within overlay image 120. For example, and without limitation, changes in color gamut 132 within overlay image 120 may indicate changes in the color within overlay image 120. In one or more embodiments, color gamut 132 may act as a reference color chart in order to determine the correct colors in processing or modification of overlay image 120.

With continued reference to FIG. 1, fixed background image 124 may include a test chart. In one or more embodiments, overlay image 120 may include a captured image of test chart. A "test chart" for the purposes of this disclosure is a specialized image or pattern used to evaluate the performance of an imaging device 156. For example, and without limitation, an image captured by an imaging device 156 of test chart may be compared to a reference of test chart wherein variations between the image and the reference may indicate the performance of the imaging device 156. In one or more embodiments, test chart may be used to determine the performance of an imaging device 156 comparing an image of test chart captured by imaging device 156 and a reference of test chart. In one or more embodiments, the performance of imaging device 156 may be determined by comparing the color profiles captured by imaging device 156 and the actual color profiles on test chat. In one or more embodiments, curvatures, geometric shapes, gray scale gradients, focus, text and the like may be compared between a captured image and test chart. In one or more embodiments, fixed background image 124 may include test chart wherein fixed background image 124 may be used to determine the quality and/or performance of imaging device 156 used to capture overlay image 120.

With continued reference to FIG. 1, fixed background image 124 may include one or more electrocardiogram (ECG) signals. As used in the current disclosure, an "electrocardiogram signal" is a signal representative of electrical activity of heart. The ECG signal may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves may provide information about the duration and regularity of various phases of the cardiac cycle. The ECG signal may help diagnose various heart conditions, such as arrhythmias, myocardial infarction (heart attack), conduction abnormalities, and electrolyte imbalances. In one or more embodiments, ECG signals may be received by one or more electrodes connected to the skin of an individual. In one or more embodiments, ECG signals may represent depolarization and repolarization occurring in the heart. In one or more embodiments, ECG signals may be captured periodically. For example, and without limitation, every second, every millisecond and the like. In one or more embodiments, ECG signals may contain an associated time variable. A "Time variable" for the purposes of this disclosure is information indicating the time at which a particular ECG signal was received. For example, and without limitation, time variable may include, 5 ms, 10 ms, 15 ms and the like. In one or more embodiments, each ECG signal may contain a time variable. In one or more embodiments, time variable may increase in given increments, such as for example, in increments of 5 ms, wherein a first time variable may include 5 ms and a second time variable may include 10 ms. In one or more embodiments, a combination of a plurality of ECG signals and correlated time variable may be used to generate a graph illustrating the heart functions of an individual. In one or more embodiments, fixed background image 124 may include a graphical representation of one or more electrocardiogram signals. In one or more embodiments, the graphical representation may be in the form of an X-Y graph. In one or more embodiments, fixed background image 124 may include one or predetermined ECG signals to be used as reference for the quality of overlay image 120. In one or more embodiments, variations in the curvature of ECG signals depicted on fixed background image 124 within overlay image 120 may indicate that overlay image 120 may have been captured poorly. In one or more embodiments, one or more ECG signals may be depicted and/or illustrated in fixed background image 124 and used to determine the performance of an imaging device 156. In one or more embodiments, fixed background image 124 may include a reference electrocardiogram signal 136. A "reference electrocardiogram signal" for the purposes of this disclosure is an ECG signal located on fixed background image 124 and used to determine the performance of an imaging device 156 which was captured an image of fixed background image 124. For example, and without limitation, a reference ECG signal 136 may be present on fixed background image 124 wherein distortion or manipulation of reference electrocardiogram signal 136 in a captured image may indicate that the image was not captured properly. In one or more embodiments, reference ECG signal 136 may be used to determine the quality of overlay image 120. In one or more embodiments, computing device 104 may identify reference ECG signal 136 wherein variations in an image captured of reference ECG signal 136 may indicate that the image was not properly captured. In one or more embodiments, fixed background image 124 may have a size of A3. Reference ECG is described further in reference to at least FIG. 2.

With continued reference to FIG. 1, overlay image 120 may include a depiction of a primary image 140 and/or a captured primary image 144. A "primary image" for the purposes of this disclosure is a physical element that conveys information in the form of a graphic and is sought to be processed by a computing device in order to extract the information. For example, and without limitation, primary image 140 may include an X-Y graph of information that may be suitable to an individual and/or computing device 104. In one or more embodiments, overlay image 120 may include a captured primary image 144. A "captured primary image" for the purposes of this disclosure captured image of fixed background image 124. For example, and without limitation, captured primary image 144 may be located within overlay image 120 wherein overlay image 120 may contain a scan or photograph of primary image 140 and/or fixed background image 124. In one or more embodiments, captured primary image 144 may include a digital representation of primary image 140 as captured by input device 152. In one or more embodiments, primary image 140 may include aa table of numerical or alphanumerical values. In one or more embodiments, primary image 140 may include a physical document, a physical image, a printed graph and the like. In one or more embodiments, primary image 140 may include a plurality of ECG signals 148. In one or more embodiments, primary image 140 may include a printout of ECG signals. In one or more embodiments, primary image 140 may include ECG sheets wherein ECG sheets include printouts of ECG signals associated with a patient. In one or more embodiments, ECG sheets may contain waves and intervals, each representing a different phase of the cardiac cycle. In one or more embodiments, primary image 140 may include a plurality of ECG signals 148 associated with a patient and/or individual of interest. In one or more embodiments, plurality of ECG signals 148 may be used by computing device 104 to make determinations about an individual's health. In one or more embodiments, plurality of ECG signals 148 and the associated primary image 140 may be received and/or generated by sensors attached to the limbs of a patient or individual. As used in this disclosure, a "sensor" is a device that may be configured to detect an input and/or a phenomenon and transmit information related to the detection. Sensor may detect a plurality of data. A plurality of data detected by sensor ay include, but is not limited to, electrocardiogram signals, heart rate, blood pressure, electrical signals related to the heart, time variables associated with captured data and the like. In one or more embodiments, and without limitation, sensor may include a plurality of sensors. In one or more embodiments, and without limitation, sensor may include one or more electrodes, and the like. Electrodes used for an electrocardiogram (ECG) are small sensors or conductive patches that are placed on specific locations on the body to detect and record the electrical signals generated by the heart. Senor may serve as the interface between the body and the ECG machine, allowing for the measurement and recording of the heart's electrical activity. A plurality of sensors may include 10 electrodes used for a standard 12-lead ECG, placed in specific positions on the chest and limbs of the patient. These electrodes are typically made of a conductive material, such as metal or carbon, and are connected to lead wires that transmit the electrical signals to the ECG machine for recording. In one or more embodiments, plurality of ECG signals 148 may be associated with a 12-lead electrocardiogram. Proper electrode placement is crucial to ensure accurate signal detection and recording. In one or more embodiments, sensors may include wireless sensors wherein data may be received from sensor to computing device 104 wirelessly. In one or more embodiments, wireless sensors may include Bluetooth enabled ECG sensors, RFID ECG sensors, Wi-Fi enabled ECG sensors and the like. In one or more embodiments, wireless sensors may allow for receipt of data from a distance. In one or more embodiments, wireless sensors may allow for a machine or system to receive data without wires connecting the sensors to computing device 104. In one or more embodiments, the presence of wires from sensors to computing device 104 may obstruct medical personnel from conducting one or more medical treatment procedures.

With continued reference to FIG. 1, the plurality of sensors may be placed on each limb, wherein there may be at least one sensor on each arm and leg. These sensors may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line. In one or more embodiments, each sensor and/or lead may contain a set of electrical signals.

With continued reference to FIG. 1, the plurality of sensors may include augmented unipolar sensors. These sensors may be labeled as aVR, aVL, and aVF. These sensors may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions. These leads capture the electrical signals from different orientations, which are then transformed into transformed coordinates to generate vectorcardiogram (VCG) representing magnitude and direction of electrical vectors during cardiac depolarization and repolarization. Transformed coordinates may include one or more a Cartesian coordinate system (x, y, z), polar coordinate system (r, θ), cylindrical coordinate system (ρ, φ, z), or spherical coordinate system (r, θ, φ). In some cases, transformed coordinates may include an angle, such as with polar coordinates, cylindrical coordinates, and spherical coordinates. In some cases, VCG may be normalized thus permitting full representation with only angles, i.e., angle traversals. In some cases, angle traversals may be advantageously processed with one or more processes, such as those described below and/or spectral analysis.

With continued reference to FIG. 1, a computing system and/or an ECG machine may generate physical printouts of the plurality of ECG signals 148 received from the sensors. In one or more embodiments, primary image 140 may include data collected from one or more sensors wherein the data depicts plurality of ECG signals 148 associated with a patient. In one or more embodiments, primary image 140 may include data in the form of a table of values, a graph in which Time is represented along the X-axis and Voltage is represented along the Y-axis and the like.

In one or more embodiments, primary image 140 may differ on each iteration of the processing of computing device 104 whereas fixed background image 124 may remain the same on each iteration. For example, and without limitation, primary image 140 may differ for each differing individual and/or patient. In another non limiting example, primary image 140 may differ for each set of data collected from a differing sensor. In one or more embodiments, primary may include a physical print depicting values of ECG signals associated with a patient. In one or more embodiments, fixed background image 124 may be used to determine the quality of primary image 140. In one or more embodiments, primary image 140 may include an ECG sheet having a size of A4 as defined by the ISO 216 standard. In one or more embodiments, fixed background image 124 may have size of A3 as defined by the ISO 216 standard.

With continued reference to FIG. 1, overlay image 120 may include captured fixed background image 128 and/or captured primary image 144. In one or more embodiments, primary image 140 may obstruct or at least partially obstruct fixed background image 124 within overlay image 120. In one or more embodiments, fixed background image 124 may include a white or blank portion reserved for primary image 140 to be placed atop fixed background image 124. In one or more embodiments, primary image 140 may lay atop fixed background image 124 wherein a portion of fixed background image 124 may be partially obstructed in overlay image 120. In one or more embodiments, primary image 140 may physically be smaller in size than that of fixed background image 124 wherein only a portion of fixed background image 124 may be obstructed when primary image 140 is placed atop fixed background image 124. In one or more embodiments, primary image 140 may be placed in front of fixed background image 124 relative to a viewer viewing overlay image 120. In one or more embodiments, primary image 140 may be placed substantially close to the center of fixed background image 124 such that a portion of the center of fixed background image 124 may be obstructed. In one or more embodiments, fixed background image 124 may act as a border to primary image 140 wherein overlay image 120 may depict primary image 140 and fixed background image 124 may border primary image 140. In one or more embodiments, overlay image 120 may include a digital image of two physical objects such as fixed background image 124 and primary image 140. In one or more embodiments, patterns, geometric shapes and the like on fixed background image 124 may still be visible within overlay image 120 while blank portions of fixed background image 124 may be obstructed by primary image 140. In one or more embodiments, overlay image 120 may be received in a digital format and suitable for processing by computing device 104.

With continued reference to FIG. 1, in one or more embodiments, overlay image 120 is received from an input device 152. An "input device" for the purposes of this disclosure is a device capable of transmitting information to computing device 104. For example, and without limitation, input device 152 may include a keyboard, a mouse, a touchscreen, a smartphone, a network server, a sensor and the like. In one or more embodiments, input device 152 may include any device capable of capturing physical information and converting the physical information into a digital format. This may include but are not limited to, imaging devices 156, sensors, cameras and the like. In one or more embodiments, input device 152 may include an imaging device 156 as described in this disclosure. An "imaging device" as described in this disclosure is a device capable of capturing still or moving images. For example, and without limitation, imaging device 156 may include a camera. In one or more embodiments, imaging device 156 may include but is not limited to, a camera, a video camera, a scanner, a fax machine and the like. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. In one or more embodiments, imaging device 156 and/or camera may be used to capture image data and/or overlay image 120. As used in this disclosure, "image data" is information representing at least a physical scene, space, and/or object. In some cases, image data may be generated by a camera. "Image data" may be used interchangeably through this disclosure with "image," where image is used as a noun. An image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively where "image" is used as a verb, in this disclosure, it refers to generation and/or formation of an image.

With continued reference to FIG. 1, input device 152 may include imaging device 156. In one or more embodiments, input device 152 may further include a transparent panel 160. A "transparent panel" for the purposes of this disclosure is a flat material capable of allowing light waves to pass through. In one or more embodiments, transparent panel 160 may include any material that contains transmissive properties, such as, but not limited to, glass or plastic. In one or more embodiments, transparent panel 160 may be used to secure and/or adhere primary image 140 to fixed background image 124. In one or more embodiments, transparent panel 160 may be used to ensure that the placement or primary image 140 with respect to fixed background image 124 does not change during a photo capture of overlay image 120. In one or more embodiments, transparent panel 160 may allow for imaging device 156 to capture primary image 140 and fixed background image 124. In one or more embodiments, fixed background image 124 may be placed atop a flat surface, wherein primary image 140 be placed atop fixed background image 124. In one or more embodiments, transparent panel 160 may then be placed atop both primary image 140 and fixed background image 124. In one or more embodiments, primary image 140 and fixed background image 124 may be capable of viewing through transparent panel 160. In one or more embodiments, transparent panel 160 may be removed and/or lifted in order to replace primary image 140 and/or fixed background image 124 following each iteration of the processing.

With continued reference to FIG. 1, input device 152 may further include a light source 164. A "light source" for the purposes of this disclosure is a device capable of emitting light. In one or more embodiments, light source 164 may include, but is not limited to, a fluorescent bulb, an LED bulb, a laser and/or any other components capable of emitting light waves. In one or more embodiments, light source 164 may be used to illuminate primary image 140 and/or fixed background image 124. In one or more embodiments, light source 164 may be situated proximal to primary image 140 and fixed background image 124 and used to reduce the effect of ambient lighting on the resulting overlay image 120. In one or more embodiments, light source 164 may be used to ensure consistent lighting during each iteration of apparatus 100. In one or more embodiments, light source 164 may be positioned directly at primary image 140 and fixed background image 124. In one or more embodiments, light source 164 may be positioned at an angle relative to transparent panel 160, primary image 140 and/or fixed background image 124 in order to reduce glare within overlay image 120. In one or more embodiments, light source 164 may be configured to illuminate primary image 140 and fixed background image 124.

With continued reference to FIG. 1, input device 152 may include imaging device 156. In one or more embodiments, imaging device 156 may be positioned proximal to transparent panel 160, wherein imaging device 156 may be configured to capture fixed background image 124 and primary image 140. In one or more embodiments, input device 152 may be used to capture overlay image 120 wherein overlay image 120 includes a captured image of fixed background image 124 and primary image 140.

With continued reference to FIG. 1, input device 152 may capture a digital image of fixed background image 124 and primary image 140. In one or more embodiments, computing device 104 may receive overlay image 120 from input device 152. In one or more embodiments, input device 152 may further include a light source 164 used to illuminate fixed background image 124 and primary image 140 and thereby capture an illuminated digital image. In one or more embodiments, the light source 164 may be used to reduce the effect of ambient lighting. In one or more embodiments, fixed background image 124 and primary image 140 may be placed beneath a transparent glass prior to capture of overlay image 120 wherein the transparent glass may act as a fixture to prevent movement of primary image 140 and fixed background image 124. Input device 152, fixed background image 124, overlay image 120 and primary image 140 are described in further detail in reference to at least FIGS. 2-3.

With continued reference to FIG. 1, computing device 104 and/or processor 108 is configured to receive overlay image 120. In one or more embodiments, computing device 104 is configured to identify captured fixed background image 128 and captured primary image 144 within overlay image 120. In one or more embodiments, the placement of captured fixed background image 128 and captured primary image 144 within overlay image 120 may remain the same wherein computing device 104 may identify fixed background image 124 and primary image 140 by using predefined parameters. In one or more embodiments, fixed background image 124 may contain reference points or fiducial markers which may be used by computing device 104 to identify captured fixed background image 128 within overly image. In one or more embodiments, computing device 104 may contain and/or receive parameters of fixed background image 124 wherein the parameters may be used to identify captured fixed background image 128. In one or more embodiments, computing device 104 may identify various markers, geometric patterns and the like that are associated with fixed background image 124. In one or more embodiments, fixed background image 124 may contain borders or markers to indicate the placement of primary image 140 atop fixed background image 124. In one or more embodiments, the borders or markers may be used to identify captured primary image 144. In one or more embodiments, computing device 104 may locate predefined patterns known to be on fixed background image 124. In one or more embodiments, computing device 104 may be programmed with a template of fixed background image 124. In one or more embodiments, the template of fixed background image 124 may indicate the location of various patterns, markers, and/or shapes on fixed background image 124. In one or more embodiments, computing device 104 may use template of fixed background image 124 in order to identify captured fixed background image 128 within overlay image 120. In one or more embodiments, computing device 104 may receive template of fixed background image 124 and identify similar patterns within overlay image 120. In one or more embodiments, computing device 104 may identify geometric shapes, distinctive colors and the like within overlay image 120 in order to identify captured fixed background image 128 and primary image 140. In one or more embodiments, fixed background image 124 may include markers, borders and the like used to identify primary image 140. For example, and without limitation, fixed background image 124 may contain a predefined border on fixed background image 124 wherein primary image 140 should be placed within the predefined borders. Computing device 104 may identify the predefined border and determine that the information within the predefined border may be primary image 140.

With continued reference to FIG. 1, computing device 104 may identify captured fixed background image 128 and captured primary image 144 within overlay image 120 using an image classifier. In one or more embodiments, processor 108 may be configured to perform image classification using an image classifier wherein processor 108 may be configured to detect various features of fixed background image 124 and/or primary image 140. An "image classifier," as used in this disclosure is a machine-learning model, such as a mathematical model, neural net, or program generated by a machine-learning algorithm known as a "classification algorithm," as described in further detail below, that sorts inputs of image information into categories or bins of data, outputting the categories or bins of data and/or labels associated therewith. Image classifier may be configured to output at least a datum that labels or otherwise identifies a set of images that are clustered together, found to be close under a distance metric as described below, or the like. Computing device 104 and/or another device may generate image classifier using a classification algorithm, defined as a process whereby computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In some cases, processor 108 may use an image classifier to identify a key image in data described in any data described in this disclosure. As used herein, a "key image" is an element of visual data used to identify and/or match elements to each other. An image classifier may be trained with binarized visual data that has already been classified to determine key images in any other data described in this disclosure. "Binarized visual data" for the purposes of this disclosure is visual data that is described in binary format. For example, binarized visual data of a photo may be comprised of ones and zeroes wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g. overlay image 120) described in this disclosure and output a key image with the data (e.g. field background image and/or primary image 140). In an embodiment, image classifier may be used to compare visual data in data such as overlay image 120 with visual data in another data set. Visual data in another data set may include a plurality of visual data retrieved from database 116. In some cases, image classifier may identify one or more components within overlay image 120 that may be unique and/or that may belong to fixed background image 124. In one or more embodiments, processor 108 may employ pattern matching techniques to identify specific patterns or abnormalities within overlay image 120 in order to identify fixed background image 124 and/or primary image 140. This can involve comparing specific segments, intervals, patterns, color gamut, and the like. Cross-correlation, template matching, or dynamic time warping algorithms may be used for this purpose. In one or more embodiments, computing device 104 and/or processor 108 may contain an existing digital image of fixed background image 124. In one or more embodiments, the existing digital image of fixed background image 124 may be compared to overlay image 120 wherein computing device 104 may compare various features within overlay image 120 and existing digital image of fixed background image 124. Similarly, computing device 104 may utilize known and repetitive features of primary image 140 in order to identify primary image 140. For example, and without limitation, while ECG signals may differ in two sets of primary images 140, the presence of X-Y coordinates, the presence of a graph in general and the like may be used to identify primary image 140. In one or more embodiments, computing device 104 may classify portions of overlay image 120 as depicting fixed background image 124 and/or primary image 140. In one or more embodiment pattern matching may include any classification processes as described in U.S. nonprovisional application Ser. No. 18/652,921, filed on May 2, 2024, entitled "AN APPARATUS AND METHOD FOR CLASSIFYING A USER TO A COHORT OF RETROSPECTIVE USERS" and the entirety of which is incorporated herein by reference. In one or more embodiments, imaging device 156 may include any imaging device and/or camera as described in U.S. nonprovisional application Ser. No. 18/653,425, filed on May 2, 2024, entitled "SYSTEMS AND METHODS FOR SIGNAL DIGITIZATION" and the entirety of which is incorporated herein by reference. In one or more embodiments, overlay image 120 and/or primary image 140 may include any images of biomedical data as described in U.S. nonprovisional application Ser. No. 18/653,235, filed on May 2, 2024, entitled "APPARATUS AND METHODS FOR IDENTIFYING ABNORMAL BIOMEDICAL FEATURES WITHIN IMAGES OF BIOMEDICAL DATA" and the entirety of which is incorporated herein by reference. In one or more embodiments, a machine learning model such as any machine learning model as described in this disclosure may include a machine learning model as described in U.S. nonprovisional application Ser. No. 18/652,364, filed on May 1, 2024, entitled "APPARATUS AND METHOD FOR TRAINING A MACHINE LEARNING MODEL TO AUGMENT SIGNAL DATA AND IMAGE DATA" and the entirety of which is incorporated herein by reference.

With continued reference to FIG. 1, computing device 104 is configured to compare captured fixed background image 128 to one or more image quality thresholds 168. An "image quality threshold" for the purposes of this disclosure is a parameter used to indicate the quality of an image captured by input device 152. For example, and without limitation, image quality threshold 168 may include a particular contrast level wherein an image exceeding or failing to meet the particular contrast level may indicate that the input device 152 failed to capture a proper image. In one or more embodiments, image quality thresholds 168 may include, loss of low contrast detail, the presence of visible spots or marks in overlay image 120, lens aberration on overlay image 120, color shifts, saturation shifts, white balance effectiveness, saturation of colors, lens distortion and the like. In an embodiments, image quality threshold 168 may indicate the maximum saturation shift that may occur in overlay image 120 based on fixed background image 124. In one or more embodiments, image quality threshold 168 may indicate the limit as to how many colors may become unsaturated in color gamut. In one or more embodiments, image quality threshold 168 may indicate the maximum range of exposure for overlay image 120 based on captured fixed background image 128 and the like. In one or more embodiments, computing device 104 may measure lighting uniformity, color moire, image noise, sharpness, exposure accuracy and ISO sensitivity, texture detail and the like. In one or more embodiments, image quality threshold 168 may indicate the maximum lighting uniformity, color moire, image noise, sharpness, exposure accuracy and ISO sensitivity, texture detail, if any. In one or more embodiments, image quality threshold 168 may be used to determine the quality of an image, such as overlay image 120, captured by input device 152. In one or more embodiments, the quality of an image may be measured by the perceived quality of fixed background image 124 within overlay image 120.

With continued reference to FIG. 1, in one or more embodiments, computing device 104 may identify various features within overlay image 120 and/or fixed background image 124 such as color distortion, exposure accuracy and ISO sensitivity, texture detail and the like as described above and compare said features to one or more image quality thresholds 168. In an embodiments, various image quality thresholds 168 may be binary. For example, and without limitation, image quality threshold 168 may indicate that any blemishes identified may indicate that the image has failed to satisfy one or more image quality thresholds 168. In one or more embodiments, image quality thresholds 168 may include a range of allowable to distortions to various shapes, patterns, grides and the like within fixed background image 124. In one or more embodiments, image quality threshold 168 may indicate a maximum distortion which may be allowed to reference ECG signal, if any. In one or more embodiments, image quality threshold 168 may indicate the maximum lens distortion, lighting uniformity, image noise and the like. In one or more embodiments, predetermined patterns on fixed background image 124 may be used to determine if overlay image 120 satisfies one or more image quality thresholds 168. For example, and without limitation, changes in geometric patterns, changes in color gamut, changes in boxes and the like may indicate satisfaction of one or more image quality thresholds 168. In one or more embodiments, patterns, geometric shapes and/or other markers on fixed background image 124 may further be used to determine the orientation of overlay image 120. In one or more embodiments, computing device 104 may determine an orientation of overlay image 120 by identifying markers within fixed background image 124 and identifying the orientation of the markers within captured fixed background image 128. In one or more embodiments, computing device 104 may measure the colors within overlay image 120 and compare them to known values that should be present within captured fixed background image 128. In one or more embodiments, computing device 104 may analyze the sharpness and/or clarity of various features on overlay image 120 and compare the sharpness and/or clarity to the actual sharpness and/or clarity of fixed background image 124. In one or more embodiments, computing device 104 may determine the range of contrast within overlay image 120 and compare that to actual values of fixed background image 124.

In one or remove embodiments, comparing fixed background image 124 to one or more image quality thresholds may include generating a two dimensional matrix of a position of one to more geometric patterns of captured fixed background image 128. In one or more embodiments, one or more edge detection and/or image detection techniques as described in this disclosure (such as in reference to at least FIG. 2) may be used to identify geometric patterns on captured fixed background image and plot geometric patterns in a two dimensional matrix. In one or more embodiments, two dimensional matrix may include a table of values indicating a position of one or more geometric patterns and/or shapes on captured fixed background image. In one or more embodiments, image quality threshold may include a two dimensional matrix of expected values of captured fixed background image 128. In one or more embodiments, image quality threshold 168 may include actual values of geometric patterns on fixed background image 124. In one or more embodiments, processor 108 may be configured to compare two dimensional matrix to image quality threshold. In one or more embodiments, a calculated rotation matrix other than 1 between two dimensional matrix and image quality threshold may indicate a rotation in captured fixed background image. In an embodiment, a skewing of values expected to be in a straight line within two dimensional matrix may indicate warping or skewing of captured fixed background image. In one or more embodiments, variation in positions within two dimensional matrix and image quality threshold 168 may indicate distortions. This may be explained in further detail in reference below in reference to at least FIG. 2.

With continued reference to FIG. 1, in one or more embodiments, image quality thresholds 168 may be generated based on known and actual values associated with fixed background images 124. For example, and without limitation, fixed background image 124 may contain known noise levels, known contrast levels, known geometric distributions wherein variations within overlay image 120 may indicate that the input device 152 did not properly capture or scan fixed background image 124. In one or more embodiments, fixed background image 124 may be generated and/or input by an individual associated with apparatus 100. In one or more embodiments, fixed background image 124 may come with an associated table of values indicating the various known parameters of fixed background image 124. In one or more embodiments, an individual associated with apparatus 100 may input image quality thresholds 168 and a range associated therewith for use by computing device 104. In one or more embodiments, computing device 104 may measure various parameters of overlay image 120 and compare said parameters to one or more image quality thresholds 168. In one or more embodiments, variations within the captured fixed background image 128 and fixed background image 124 may indicate issues with the input device 152 or the capturing process.

In one or more embodiments, fixed background image 124 may contain an associated fixed reference image 172. A "fixed reference image" for the purposes of this disclosure is a digital copy of fixed background image 124. In one or more embodiments, fixed reference image 172 may be digitally generated. In one or more embodiments, fixed reference image 172 may include a digital replica or copy of fixed background image 124. In one or more embodiments, fixed reference image 172 may be used to print or produce fixed background image 124. In one or more embodiments, processor 108 may be configured to compare overlay image 120 and/or captured fixed background image 128 and compare various parameters of captured fixed background image 128 to fixed reference image 172. In one or more embodiments, changes in color saturation, changes in distortion, changes in contrast and the like may indicate poor capture quality by input device 152. In one or more embodiments, comparing captured fixed background image 128 to one or more image quality thresholds 168 may include comparing captured fixed background image 128 to fixed reference image 172. In one or more embodiments, captured fixed background image 128 within overlay image 120 may be compared to fixed reference image 172. In one or more embodiments, fixed reference image 172 may be generated by an individual associated with apparatus 100, received from a $3^{rd}$ party, retrieved from a database 116 and the like.

With continued reference to FIG. 1, computing device 104 is configured to determine an image quality score 176. An "image quality score" for the purposes of this disclosure is a determination as to whether overlay image 120, or the contents captured therein, are suitable for use. For example, and without limitation, image quality score 176 may indicate that overlay image 120 contains poor image quality, and as a result, the contents therein (e.g. primary image 140) cannot be used for further processing. In one or more embodiments, image quality score 176 may be determined by the comparison of overlay image 120 and/or captured fixed background image 128 to one or more image quality thresholds 168. In one or more embodiments, image quality score 176 may be binary wherein image quality score 176 may indicate if overlay image 120, and the contents there are suitable for use. In one or more embodiments, image quality score 176 may be numerical wherein image quality score 176 may be calculated based on adherence of fixed background image 124, or alternatively overlay image 120, to one or more image quality thresholds 168. In one or more embodiments, a determination of the quality of fixed background image 124 within overlay image 120 may be used as a determination of the quality of primary image 140. In one or more embodiments, processor 108 may determine image quality score 176 of captured primary image 144 as a function of captured fixed background image 128 and/or captured fixed background image 128 within overlay image 120. In one or more embodiments, image quality score 176 may be used to determine if captured primary image 144 may be suitable for use by computing device 104. In one or more embodiments, captured primary image 144 may be suitable for further processing by computing device 104. In one or more embodiments, variations in captured fixed background image 128 may be indicative of variations within captured primary image 144.

With continued reference to FIG. 1, processor 108 is configured to output an image modification datum 180 as a function of at least image quality score 176. An "image modification datum" for the purposes of this disclosure is information that can be used to increase the quality of overlay image 120. For example and without limitation image modification datum 180 may include instructions to reduce lighting on light source 164, to change the angle of imaging device 156 positioned at primary image 140 and the like. In one or more embodiments, image modification datum 180 may be used to modify one or more components within input device 152 in order to capture a better image of overlay image 120. In one or more embodiments, image modification datum 180 may include steps and/or instructions, such as but not limited to, instructions to increase light intensity, decrease light intensity, increase light warmth, change the angle of imaging device 156, change the aperture of imaging device 156 and the like. In one or more embodiments, image modification datum 180 may include information indicating that a blemish, crease and/or a dust particle was identified on fixed background image 124 and as a result, needs to be removed. In one or more embodiments, image modification datum 180 may further include steps and/or instructions needed to digitally modify overlay image 120 in order for overlay image 120 to receive a higher and/or valid image quality score 176. In one or more embodiments, image modification datum 180 may include instructions in order to digitally alter overlay image 120 such as but not limited to, changing the contrast of overlay image 120, changing the brightness, changing the exposure, changing highlights, changing the warmth, changing the sharpness and the like. In one or more embodiments, image modification datum 180 may include one or more instructions in order for overlay image 120 and/or captured fixed background image 128 to satisfy one or more image thresholds. In one or more embodiments, image modification datum may be determined by changes in two dimensional matrix in comparison to image quality thresholds 168 and/or expected values. In an embodiments, changes in two dimensional matrix may be correlated with a degree of change for one or more parameters of imaging device. for example, and without limitation, values in a rotation matrix may indicate the amount of rotation needed to fix imaging device. In another non-limiting example, changes in the positioning of geometric patterns may indicate a relative degree of change needed for fixing distortion of imaging device.

With continued reference to FIG. 1, image modification datum 180 may further include image modification parameters 184 for input device 152. "Image modification parameters" for the purposes of this disclosure is information associated with the configurable settings 186 of input device 152. For example, and without limitation image modification parameter 184 may refer to the aperture level on input device 152 wherein the aperture level may be configured to allow for the increase or decrease of light. In one or more embodiments, image modification parameter 184 may include instructions and commands to modify at least one configurable setting 186 on input device 152. A "configurable setting" for the purposes of this disclosure is an option within a device or system that can be adjusted in order to alter how the system or device behaves or performs. For example, and without limitation, configurable setting 186 may include aperture levels, light intensity, light warmth, resolution and the like. In an embodiments, each configurable setting 186 of input device 152 may affect the quality of overlay image 120. In an embodiments, modification of each or any configurable setting 186 on input device 152 may affect the resulting product (e.g. overlay image 120). In one or more embodiments, image modification parameters 184 may include, but are not limited, the distance of light source 164, the orientation of light source 164, the type of light emitted, the aperture level, the contrast of imaging device 156 and the like. In an embodiment, image modification parameters 184 may include any components of input device 152 that may be configured in order to increase the quality of overlay image 120. In one or more embodiments, image modification parameters 184 may indicate the correct orientation of imaging device 156, the correct orientation of light source 164, the correct brightness intensity, the correct distance of imaging device 156 to transparent panel 160 and the like. In one or more embodiments, image modification parameters 184 may include information associated resolution of imaging device 156, focus of imaging device 156, the ISO settings on imaging device 156, the aperture settings on imaging device 156, the lens quality of imaging device 156, and the like. In one or more embodiments, image modification parameters 184 may indicate to an individual the particular settings of input device 152 that need to be configured in order to produce a more suitable overlay image 120. In one or more embodiments, image modification parameters 184 may include code and/or instructions which may be transmitted to input device 152 and adjusted by computing device 104. In one or more embodiments, one or more components of input device 152 may be communicatively connected to computing device 104 and/or processor 108. In one or more embodiments, computing device 104 may communicate with input device 152 to adjust variables that can be adjusted through electronic communication. This may include, but is not limited to, light intensity, camera resolution, ISO settings and the like. In one or more embodiments, light source 164 and/or may be coupled to one or more actuators and/or electric motors wherein computing device 104 may transmit commands to the actuators and/or electric motors to adjust the distance and orientation of imaging device 156 and/or input device 152.

In one or more embodiments, image modification parameters 184 may be generated as a function of the one or more image quality thresholds 168. In an embodiments, failure to satisfy a particular image quality threshold 168 may indicate a particular image modification parameter 184. For example, and without limitation, in instances overlay image 120 fails to satisfy an image quality threshold 168 associated with brightness, image modification parameter 184 may include instructions to adjust brightness. In one or more embodiments, various parameters within overlay image 120 may be quantified wherein failing to meet or exceeding a particular threshold may be directly related and proportional to a particular image modification parameter 184. For example, and without limitation, failing to meet a brightness standard by a numerical value of 10 may indicate to computing device 104 to increase or decrease the light intensity of light source 164 by a particular amount. In one or more embodiments, image modification parameters 184 may be directly proportional and/or linearly associated with image quality thresholds 168. In one or more embodiments, larger deviations from image quality thresholds 168 may result in larger deviations in image modification parameters 184.

With continued reference to FIG. 1, image modification datum 180 may be linearly and/or proportionally related to deviations in image quality thresholds 168. In an embodiment failure to satisfy a particular image quality threshold 168 may result in the generation or determination of image modification datum 180 while the intensity of the deviation from the image quality threshold 168 may indicate the intensity of the image modification datum 180. In one or more embodiments, an individual associated with apparatus 100 may populate a table having a plurality of image modification datum 180 wherein each image modification datum 180 is associated with a particular image quality threshold 168. In one or more embodiments, failure to satisfy a particular image quality threshold 168 may result in the generation or selection of the associated image modification datum 180. In one or more embodiments, image modification datum 180 may contain variables that adjust accordingly based on the deviation from an image quality threshold 168. In an embodiment, a larger deviation from a particular image quality threshold 168 may result in a larger intensity of a particular image modification datum 180. For example, and without limitation, an image modification datum 180 may indicate to increase brightness by +10 or +50 depending on the deviation of a particular image quality threshold 168.

With continued reference to FIG. 1, image modification datum 180 may be generated as a function of a machine learning model. In one or more embodiments, computing device 104 may include a machine learning module to implement one or more algorithms or generate one or more machine-learning models to generate outputs. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from database 116, user inputs and/or be provided by a user. In other embodiments, a machine-learning module may obtain a training set by querying a communicatively connected database 116 that includes past inputs and outputs. Training data may include inputs from various types of databases, resources, libraries, dependencies and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to categories by tags, tokens, or other data elements. A machine learning module may be used to create a machine learning model and/or any other machine learning model using training data. Training data may be data sets that have already been converted from raw data whether manually, by machine, or any other method. In some cases, the machine learning model may be trained based on user input. For example, a user may indicate that information that has been output is inaccurate wherein the machine learning model may be trained as a function of the user input. In some cases, the machine learning model may allow for improvements to computing device 104 such as but not limited to improvements relating to comparing data items, the ability to sort efficiently, an increase in accuracy of analytical methods and the like.

With continued reference to FIG. 1, in one or more embodiments, a machine-learning module may be generated using training data. Training data may include inputs and corresponding predetermined outputs so that machine-learning module may use the correlations between the provided exemplary inputs and outputs to develop an algorithm and/or relationship that then allows machine-learning module to determine its own outputs for inputs. Training data may contain correlations that a machine-learning process may use to model relationships between two or more categories of data elements. The exemplary inputs and outputs may come from a database 116, and/or be provided by a user. In other embodiments, machine-learning module may obtain a training set by querying a communicatively connected database 116 that includes past inputs and outputs. Training data may include inputs from various types of databases, resources, libraries, dependencies and/or user inputs and outputs correlated to each of those inputs so that a machine-learning module may determine an output. Correlations may indicate causative and/or predictive links between data, which may be modeled as relationships, such as mathematical relationships, by machine-learning processes, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. In one or more embodiments, A machine learning model such as modification machine learning model 188 may include a machine learning model configured to receive inputs such as image quality score 176 and output one or more image modification datum 180.

With continued reference to FIG. 1, apparatus 100 may include a modification machine learning model 188. modification machine learning model 188 may include any machine learning model as described in this disclosure. In one or more embodiments, modification machine learning model 188 may be configured to receive input such as image quality score 176 and output image modification datum 180. In an embodiments, a particular image quality score 176 may be correlated to one or more image modification datum 180. In one or more embodiments, modification machine learning model 188 may be trained with modification training data 190. In one or more embodiments, modification training data 190 may include a plurality of image quality scores 176 correlated to a plurality of image modification datum 180. In an embodiment, each image quality score 176 may be correlated to one or more image modification datum 180. In one or more embodiments, modification training data 190 may be generated by an individual wherein an individual may receive a set of overlay images 120, image quality scores 176 and the like and assign one or more image modification datum 180. In one or more embodiments, modification training data 190 may be generated by a user, 3$^{rd}$ party, retrieved from a database 116 and the like. In one or more embodiments, modification training data 190 may include a plurality of overlay images 120 and/or a plurality of captured fixed background images 128 correlated to a plurality of image modification datum 180. In one or more embodiments, modification training data 190 may be used to train modification machine learning model 188.

In one or more embodiments, a machine learning model such as modification machine learning model 188 may contain parameter values. "Parameter values" for the purposes of this disclosure are internal variables that a machine learning model has generated from training data in order to make predictions. In one or more embodiments, parameter values may be adjusted during pretraining or training in order to minimize a loss function. In one or more embodiments, during training, predicted outputs of the machine learning model are compared to actual outputs wherein the discrepancy between predicted output and actual outputs are measured in order to minimize a loss function. A loss function also known an "error function" may measure the difference between predicted outputs and actual outputs in order to improve the performance of the machine learning model. A loss function may quantify the error margin between a predicted output and an actual output wherein the error margin may be sought to be minimized during the training process. The loss function may allow for minimization of discrepancies between predicted outputs and actual outputs of the machine learning model. In one or more embodiments, the loss function may adjust parameter values of the machine learning model. In one or more embodiments, in a linear regression model, parameter values may include coefficients assigned to each feature and the bias term. In one or more embodiments, in a neural network, parameter values may include weights and biases associated with the connection between neurons or nodes within layers of the network. In one or more embodiments, during pretraining and/or training of the machine learning model, parameter values of the machine learning model (e.g. modification machine learning model 188) may be adjusted as a function of at least one output of the machine learning model. In one or more embodiments, processor 108 may be configured to minimize a loss function by adjusting parameter values of modification machine learning model 188 based on discrepancies between outputs and feedback associated with said outputs. In one or more embodiments, training modification machine learning model 188 may include adjusting one or more parameter values of modification machine learning model 188 based on feedback received.

With continued reference to FIG. 1, processor 108 may be configured to generate an updated overlay image 192 as a function of the image modification datum 180. "Updated overlay image" for the purposes of this disclosure refers to a secondary capture of overlay image 120 or a modification of overlay image 120 following implementation of one or more image modification datum 180. For example, and without limitation, updated overlay image 192 may include overlay image 120 following adjustment of a resolution on input device 152. In one or more embodiments, updated overlay image 192 may include overlay image 120 that has been captured using better lighting, differing camera angles, differing resolution, differing aperture levels, the removal of blemishes and the like. In one or more embodiments, computing device 104 may automatically adjust configurable settings 186 on input device 152 based on generation of image modification datum 180. Additionally or alternatively, computing device 104 may instruct a user of apparatus 100 to adjust various configurable settings 186 of input device 152 prior to capture of updated overlay image 192. In one or more embodiments, overlay image 120 may be digitally modified wherein updated overlay image 192 may include modification made to overlay image 120. This may include, but is not limited to, changes to contrast, changes to brightness, changes to exposure levels and the like. In one or more embodiments, computing device 104 may use an image modification software to modify parameters of overlay image 120 to generate updated overlay image 192. In one or more embodiments, updated overlay image 192 may include an updated fixed background image 194 and an updated primary image 196. An "updated fixed background image" for the purposes of this disclosure is a captured image of fixed background image 124 within updated overlay image 192. Similarly, an "updated primary image" for the purposes of this disclosure is a captured image of primary image 140 within updated overlay image 192. In one or more embodiments, computing device 104 may be configured to capture update overlay image 120, wherein updated overlay image 192 may include an image adhering to various image quality thresholds 168. In one or more embodiments, computing device 104 may identify updated fixed background image 194 and updated primary image 196, compare updated fixed background image 194 to one or more image quality thresholds 168, generate an image quality score 176 and generate image modification datum 180 if needed. In one or more embodiments, computing device 104 may be configured to iteratively generate updated overlay image 192 until updated overlay image 192 includes an image suitable for processing.

With continued reference to FIG. 1, modification machine learning model 188 may be configured to iteratively generate image modification datum 180 wherein computing device 104 may generate updated overlay image 192 and iteratively generate image modification datum 180 until updated overlay image 192 is suitable for processing. In one or more embodiments, modification machine learning model 188 may be configured to iteratively generate image modification datum 180 as a function of modification machine learning model 188, modification training data 190 and/or image quality score 176. In one or more embodiments, computing device 104 may be configured to iteratively generate updated overlay image 192 until a suitable quality of updated overlay image 192 is generated. In one or more embodiments, computing device 104 may iteratively determine an updated image quality score 198 of updated primary image 196, updated fixed background image 194 and the like. An "updated image quality score" for the purposes of this disclosure is image quality score 176 generated for updated overlay image 192. In one or more embodiments, updated image quality score 198 may be iteratively generated until a suitable updated image quality score 198 is generated. In one or more embodiments, updated quality score may be used to train modification machine learning model 188. In an embodiments, updated image quality score 198 may serve as feedback to modification machine learning model 188 wherein positive changes to updated image quality in comparison to image quality score 176 may indicate accurate outputs, while negative changes to updated image quality score 198 in comparison to image quality score 176 may indicate inaccurate outputs. In one or more embodiments, updated image quality score 198 may be used to modify parameter values of modification machine learning model 188 such that outputs are more accurate in future iterations. In one or more embodiments, modification machine learning model 188 may be self-supervised wherein the accuracy of outputs may be determined using updated image quality score 198.

With continued reference to FIG. 1, primary image 140 may be used within one or more machine learning models to make one or more determinations about a patient. In an embodiment, primary image 140 and/or captured primary image 144 may indicate various cardiac abnormalities associated with a patient wherein modifications and/or distortions to primary image 140 may yield inaccurate outputs. In one or more embodiments, image quality score 176 and/or image modification datum 180 may minimize the amount of inaccurate outputs. In one or more embodiments, computing device 104 may determine the quality of captured fixed background image 128 and make one or more determinations on captured primary image 144. In one or more embodiments, captured primary image 144 may be used to train one or more machine learning models. In one or more embodiments, a plurality of captured primary images 144 may be created wherein the plurality of captured primary images 144 may be used as training data in one or more machine learning models. In one or more embodiments, captured primary image 144 may be used as an input in ECG machine learning model and/or ECG machine learning model as described in U.S. nonprovisional application Ser. No. 18/641,217, filed on Apr. 19, 2024, entitled "SYSTEMS AND METHODS FOR TRANSFORMING ELECTRO-CARDIOGRAM IMAGES FOR USE IN ONE OR MORE MACHINE LEARNING MODELS" and the entirety of which is incorporated herein by reference.

Figure 2:
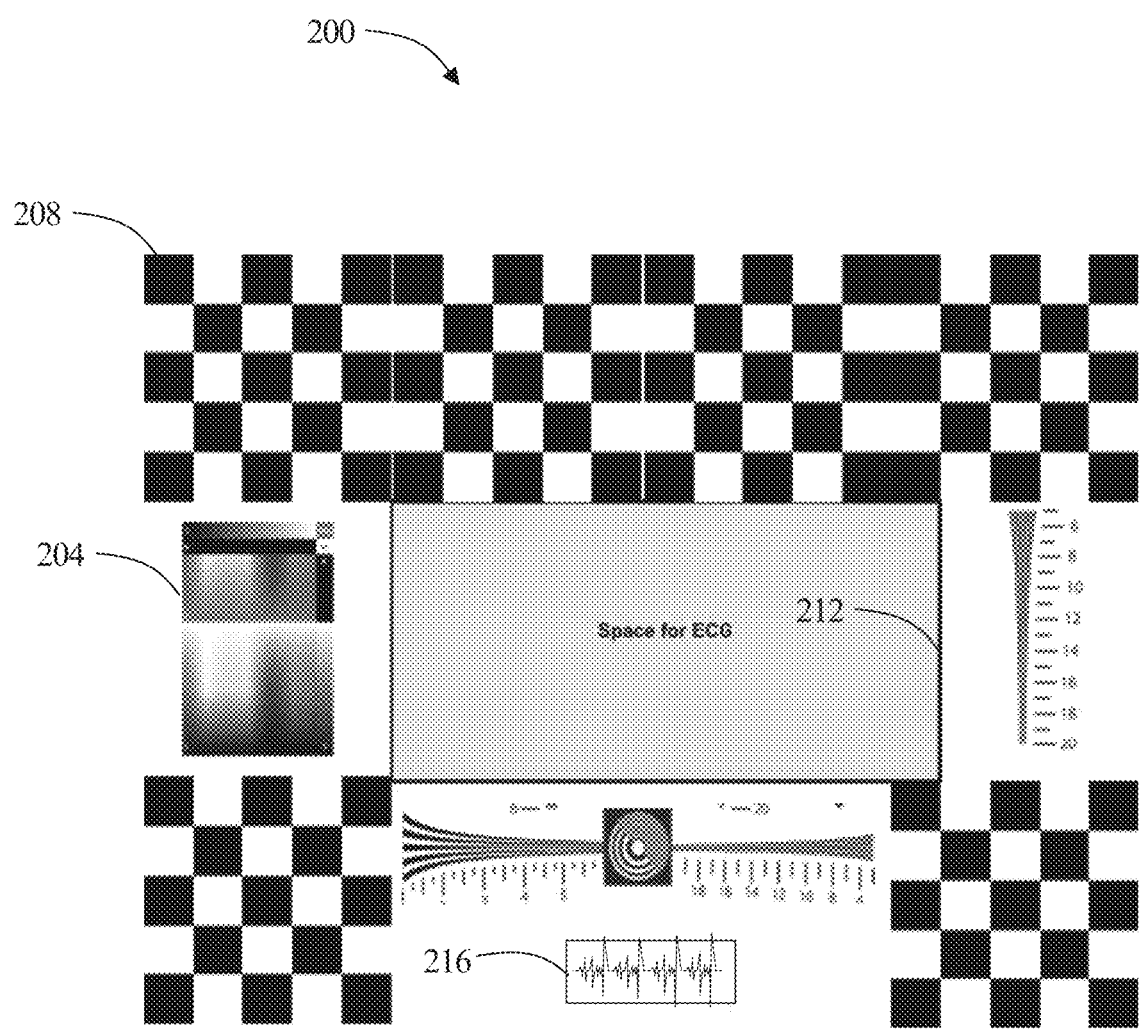
FIG. 2 is an exemplary embodiment of a fixed background image.

Referring now to FIG. 2, an exemplary embodiment of a fixed background image 200 is described. In one or more embodiments, fixed background image 200 may serve as a test sheet in order to determine the quality of a photograph or a scan captured by an imaging device. In one or more embodiment, fixed background image 200 may allow computing device and/or an individual to determine if a photo was captured with proper lighting, with proper contrast, with proper color output and the like. In one or more embodiments, fixed background image 200 may include a color gamut 204 which may be used to determine if the color output of a captured image has been captured correctly. In one or more embodiments, fixed background image 200 may include geometric patterns 208. In one or more embodiments, geometric patterns may be used to determine if distortion has occurred if contrast has been distorted and the like. In one or more embodiments, the geometric patterns may be used to figure out the intrinsic (focal length, optical center) and extrinsic parameters of an imaging device (e.g. rotation and translation of the camera) as well as distortion caused due to paper or lens used. In one or more embodiments, an imaging device may capture a test sheet, such as fixed background image and identify corners of geometric patterns such as black and white squares. In one or more embodiments, identifying corners allows the computing device to identify the positions of the black and white squares. These positions may then be compared to the actual positions of the geometric patterns on fixed background image 200. In one or more embodiments, comparison between actual and identified positions of geometric patterns using optimization techniques such as Levenberg-Marquardt algorithms can be used to determine the imaging device's focal length, optical center, distortion coefficients, rotation and the like. In one or more embodiments, processor 108 may use one or more machine vision systems in order to identify geometric patterns and/or colors in fixed background image 200. For example, in some cases a machine vision system may be used for world modeling or registration of objects within a space such as fixed background image 200. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative to a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and ø may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure. In one or more embodiments, processor 108 may be configured to determine focal length by using known sizes and structures of geometric patterns and how they are projected onto an image. In one or more embodiments, processor may compute distortion coefficients by identifying deviations in patterns on fixed background image in comparison to their expected positions. In one or more embodiments, distortion coefficients may include radial distortion which account for barrel r pincushion distortion wherein points are displaced radially from a center. In one or more embodiments, distortion coefficients may include tangential coefficients in which lens misalignment may include points to be displaced tangentially. In one or more embodiments, one or more edge detection algorithms as described above may be used to identify the locations of various geometric patterns. In one or more embodiments, processor may use one or more edge detection techniques to identify grids, patterns and the like within fixed background image. In one or more embodiments, processor may define corresponding points for each pattern on fixed background image based on their relative position on fixed background image. In one or more embodiments, processor may generate a matrix of points wherein changes in the matrix to expected values in order to determine focal length, distortion coefficients and the like.

With continued reference to FIG. 1, features on fixed background image 200 such as corners or dots across multiple geometric patterns may be used to determine focal length. In one or more embodiments, processor may use 3d coordinates of various features and their 2D projections in an image plane in order to determine focal length. In one or more embodiments, optical center may be determined by finding a point in an image plan in which the optical axis intersects. This may be done by minimizing reprojection error for detected features. In one or more embodiments, distortion coefficients may be determined by comparing the positions of various detect features on fixed background image to their expected positions. Changes between actual and expected positions may indicate a distortion. In one or more embodiments, one or more feature detection algorithms (e.g. edge detection) may be used to detect various features. In one or more embodiments, processor may generate a 2D matrix of the detected features. In one or more embodiments, processor may be configured to compare the actual matrix to an expected matric in order to find the rotation matrix which may be used to determine rotation of an imaging device.

With continued reference to FIG. 1, one or more edge detection techniques may be used in order to generate a two dimensional matrix of a position of geometric features on fixed background image 200. In one or more embodiments, focal length may be determined by projecting three dimensional object points into a two dimensional image plane and identifying variations between actual and expected values. In one or more embodiments, optical center may be found by averaging projected image points on the matrix and minimizing reprojection error. In one or more embodiments, distortion coefficients may be determined by determining a skew of various points within the two dimensional matrix. For example, and without limitation, processor may identify points that should be in a straight line, yet the two dimensional matrix indicates that the points are skewed. In one or more embodiments, rotation of imaging device by determining a rotation matrix between actual values and expected values which two matrices. In one or more embodiments, brightness may be determined by calculating the average intensity of all pixels within an image and comparing it to actual values. In one or more embodiments, contrast may be determined by calculating a standard deviation of o pixel intensities and comparing them to known values. In one or more embodiments, color correction may be determined by determining how much gain should be applied to presumably white pixel in order to make them white.

With continued reference to FIG. 1, in one or more embodiments, color gamut's on fixed background image may be used to correct deviations in known values on fixed background image. In one or more embodiments, a computing device may compare captured colors on color gamut to actual colors on color gamut. Deviations between actual colors and captured colors may indicate deviations in the settings of the imaging device. In one or more embodiments, computing device may create a color profile in order to correct deviations and ensure accurate color reproduction. In one or more embodiments, geometric patterns on fixed background image 200 may be used to detect points in fixed background image and compare the distance between points in the captured image and the distance between points in fixed background image 200. In one or more embodiments, changes in the waves, distances, and the like of reference ECG signal 216 and a captured image of reference ECG signal 216 may contain that warping has occurred on the image. In one or more embodiments, fixed background image 200 may contain a demarcation 212. In one or more embodiments, the demarcation 212 may be used to instruct an individual as to where an image (such as primary image as described above) may be placed prior to capture of fixed background image 200. In one or more embodiments, demarcation 212 may illustrate the borders on which an image or graphical illustration may be placed. In one or more embodiments, fixed background image 200 may include an ECG reference Signal 216. In one or more embodiments, ECG reference signal 216 may include numbers, waves, and the like. In one or more embodiments, ECG reference signal 216 may be used to determine if distortions have occurred in an image of fixed background image 200. In one or more embodiments, changes in the curve, lengths, waves and the like of ECG reference signal 216 may indicate that information may not be properly extracted from the image.

With continued reference to FIG. 2, various image quality check parameters may be used to ensure that an image captured of fixed background image is suitable for processing. In one or more embodiments, a computing device may detect artifacts by analyzing the captured image for inconsistencies or distortions in low contrast areas. Edge detection algorithms or comparison between the captured image with a reference image may be used to identify any loss of detail. In one or more embodiments, detection of artifacts may indicate that the compression settings or noise reduction settings on an imaging device require adjustment. In one or more embodiments, blemishes may be identified within captured fixed background image by detecting irregularities or anomalies. Image processing algorithms can be used to identify and classify these anomalies based on their size, shape, or intensity. In one or more embodiments, the presence of blemishes may indicate the lens of the imaging device may be dirty. In one or more embodiments, color accuracy can be determined by comparing the captured image with a reference color chart or color profile. Algorithms may analyze the color values in the image and measure the differences between the captured colors and the expected colors. In one or more embodiments, changes in color accuracy may indicate that the white balance settings or color calibration settings of imaging device require adjustment. In one or more embodiments, lens distortion of imaging device may be identified by identifying distortions within fixed background image 200. This may include identifying straight lines and/or known patterns and measuring deviations. In one or more embodiments, correction of lens distortion may require using lenses with differing distortion characteristics. In one or more embodiments, detecting of lens flare and/or light flickering may indicate the position, angle and/or lens used on imaging device may require modification. In one or more embodiments, the use of anti-aliasing filters may be used to reduce or eliminate color moire effects.

Figure 3:
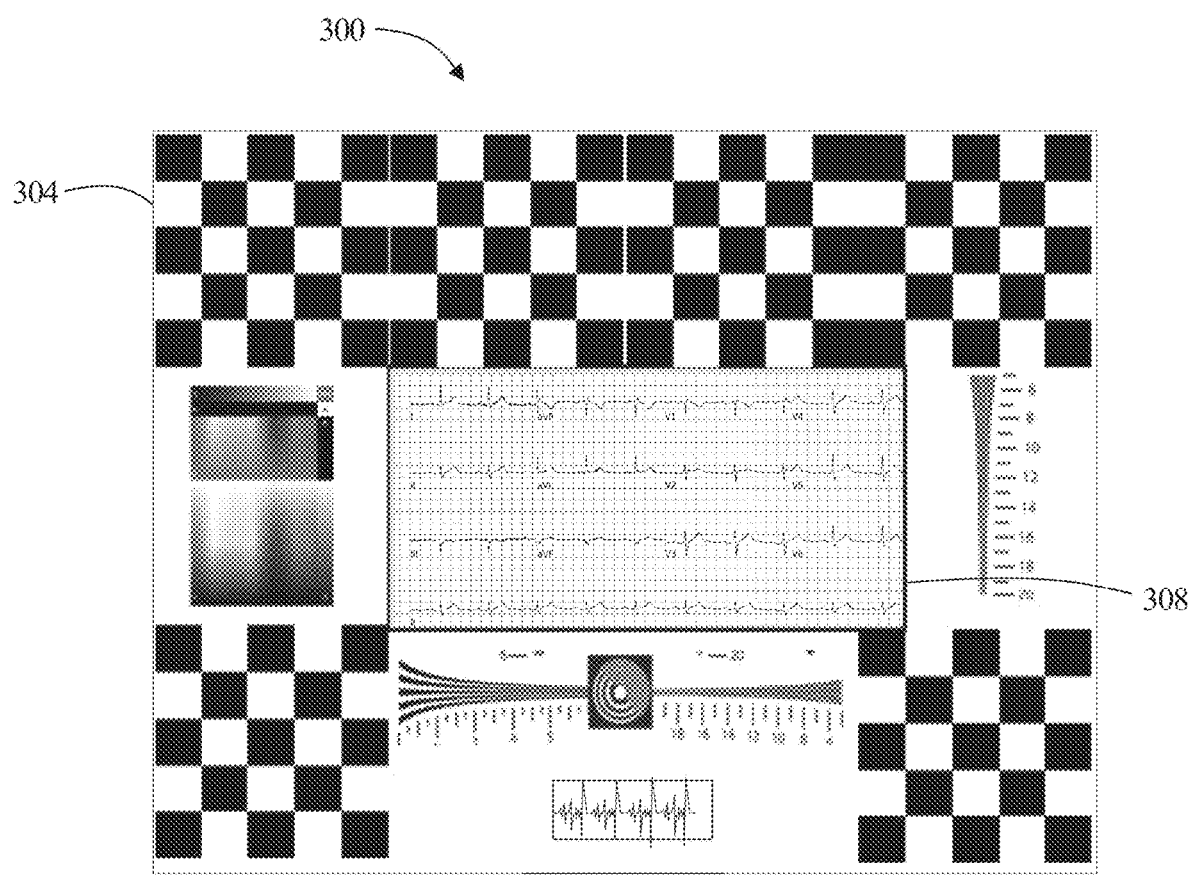
FIG. 3 is an exemplary embodiment of an overlay image.

Referring now to FIG. 3, an exemplary embodiment of an overlay image 300 is described. In one or more embodiments, overlay image may include an overlay image 300 as described in this disclosure. In one or more embodiments, overlay image 300 may include an image captured by an imaging device as described in this disclosure. In one or more embodiments, overlay image may include an image of fixed background image 304. In one or more embodiments, overlay image may further include an image of primary image 308. In one or more embodiments, primary image may include a graphical illustration of ECG signals. In one or more embodiments, primary image may include a printout of ECG signals received from an ECG machine. In one or more embodiments, a computing device may receive overlay image 300 and determine if overlay image was captured properly. In one or more embodiments, a computing device as described above may compare fixed background image 304 within overlay image 300 to image quality thresholds in order to determine the quality of overlay image 300. In one or more embodiments, in instances in which image of fixed background image 304 satisfies one or more image quality thresholds, image of primary image 308 may be determined to be suitable for use.

Figure 4:
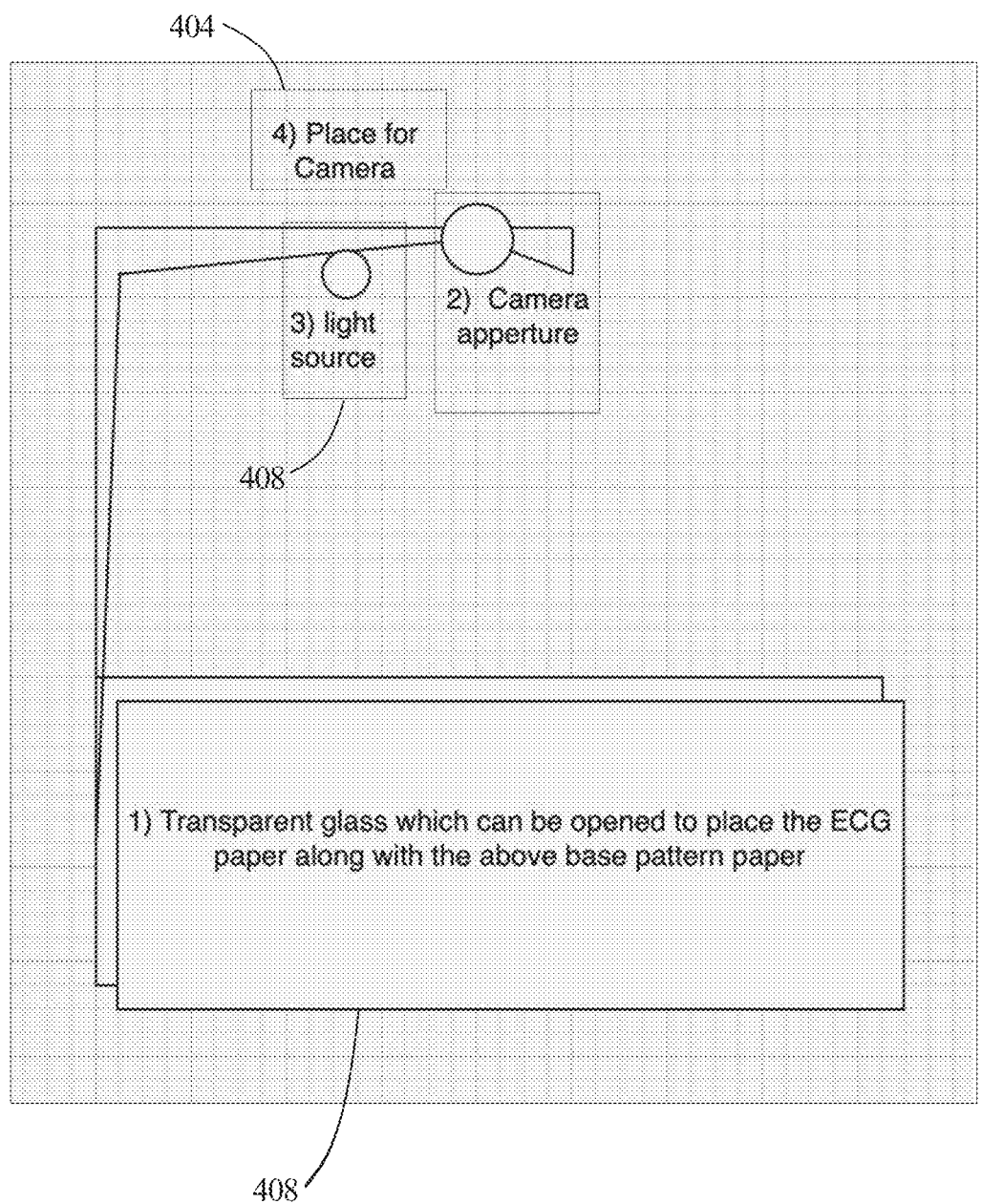
FIG. 4 is an exemplary embodiment of a schematic for capturing images.

Referring now to FIG. 4, a schematic 400 for capturing images is described. In one or more embodiments, schematic 400 may be used to capture overlay image as described above. In one or more embodiments, schematic may include the use of input device as described above. In one or more embodiments, schematic may include the use of an imaging device 404, such as a camera. In one or more embodiments, schematic may include a light source 408. In one or more embodiments, light source may allow for the illumination of light onto an object that is sought to be captured. In one or more embodiments, schematic 400 may further include a transparent panel 412. In one or more embodiments, transparent panel 412 may be configured to secure an object of interest in place. In one or more embodiments, the objects of interest may include fixed background images and/or primary images.

Figure 5:
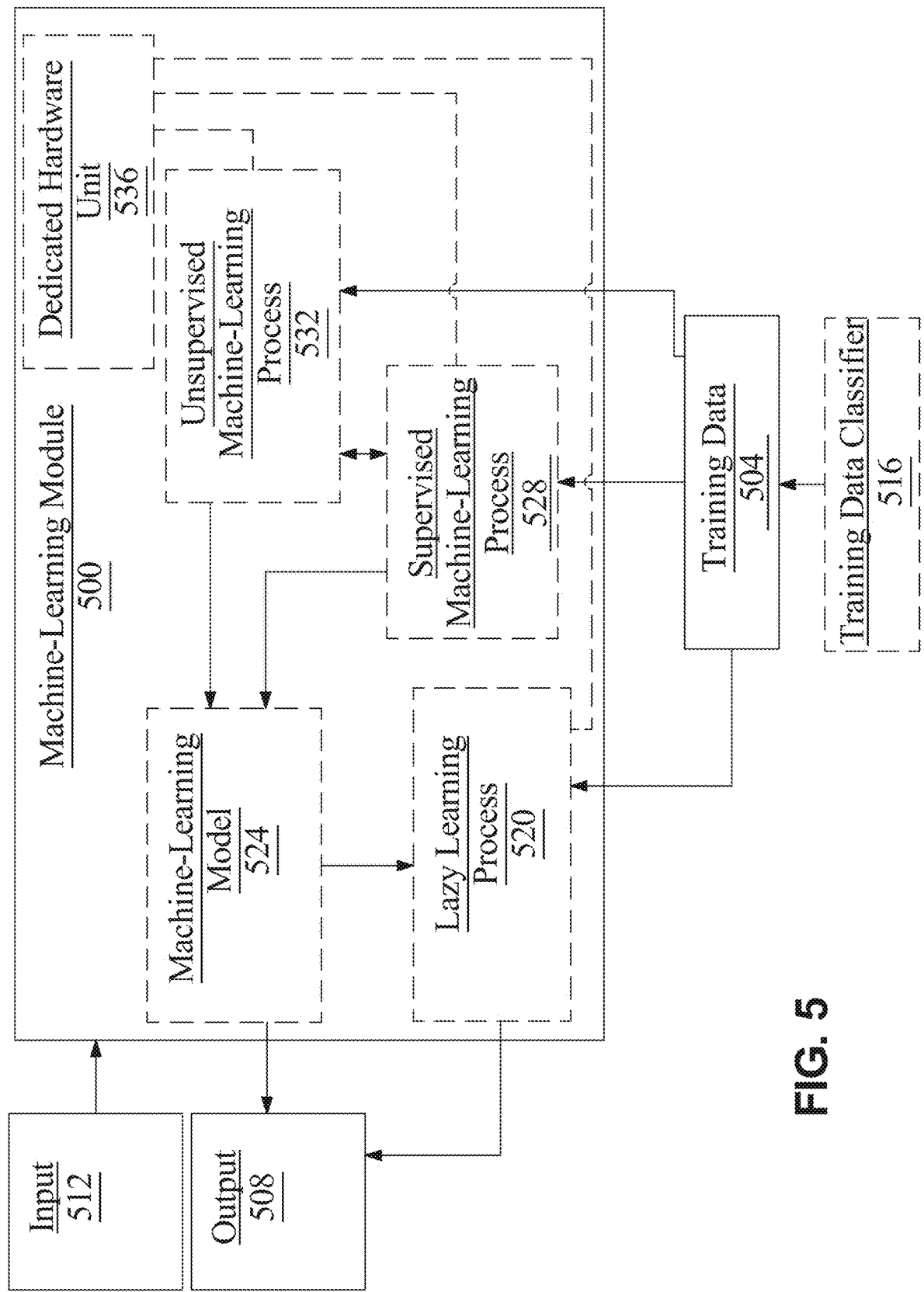
FIG. 5 is a block diagram of an exemplary machine-learning process.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs may include inputs such as image quality scores, overlay images and the like whereas outputs may include outputs such as image modification datum.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to classes associated with image quality thresholds. For example, and without limitation, elements may be classified to classes of images having low brightness, classes of images having high contrast and the like.

Still referring to FIG. 5, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 5, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 5, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 5, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 5, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 5, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 5, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} - \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 5, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs such as overlay images, updated overlay images, updated image quality scores, image quality scores and the like as described above as inputs, image modification datum and/or updated image modification datum as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus 100, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus 100, and/or method described in this disclosure; such examples may be modified and/or labeled according to user feedback or other processes to indicate desired results, and/or may have actual or measured results from a process being modeled and/or predicted by system, module, machine-learning model or algorithm, apparatus 100, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus 100, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 6:
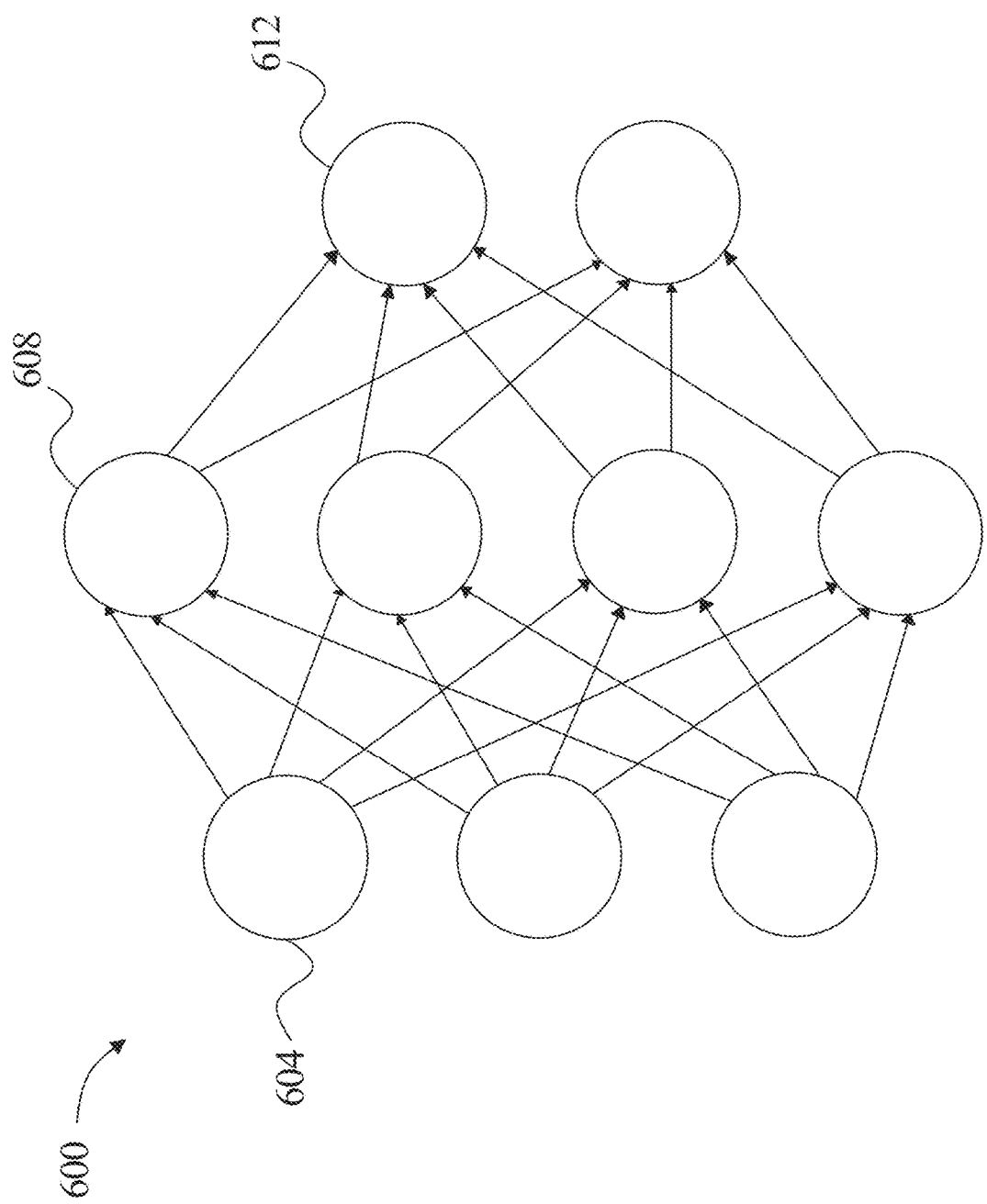
FIG. 6 is a diagram of an exemplary embodiment of a neural network.

Referring now to FIG. 6, an exemplary embodiment of neural network 600 is illustrated. A neural network 600 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 7:
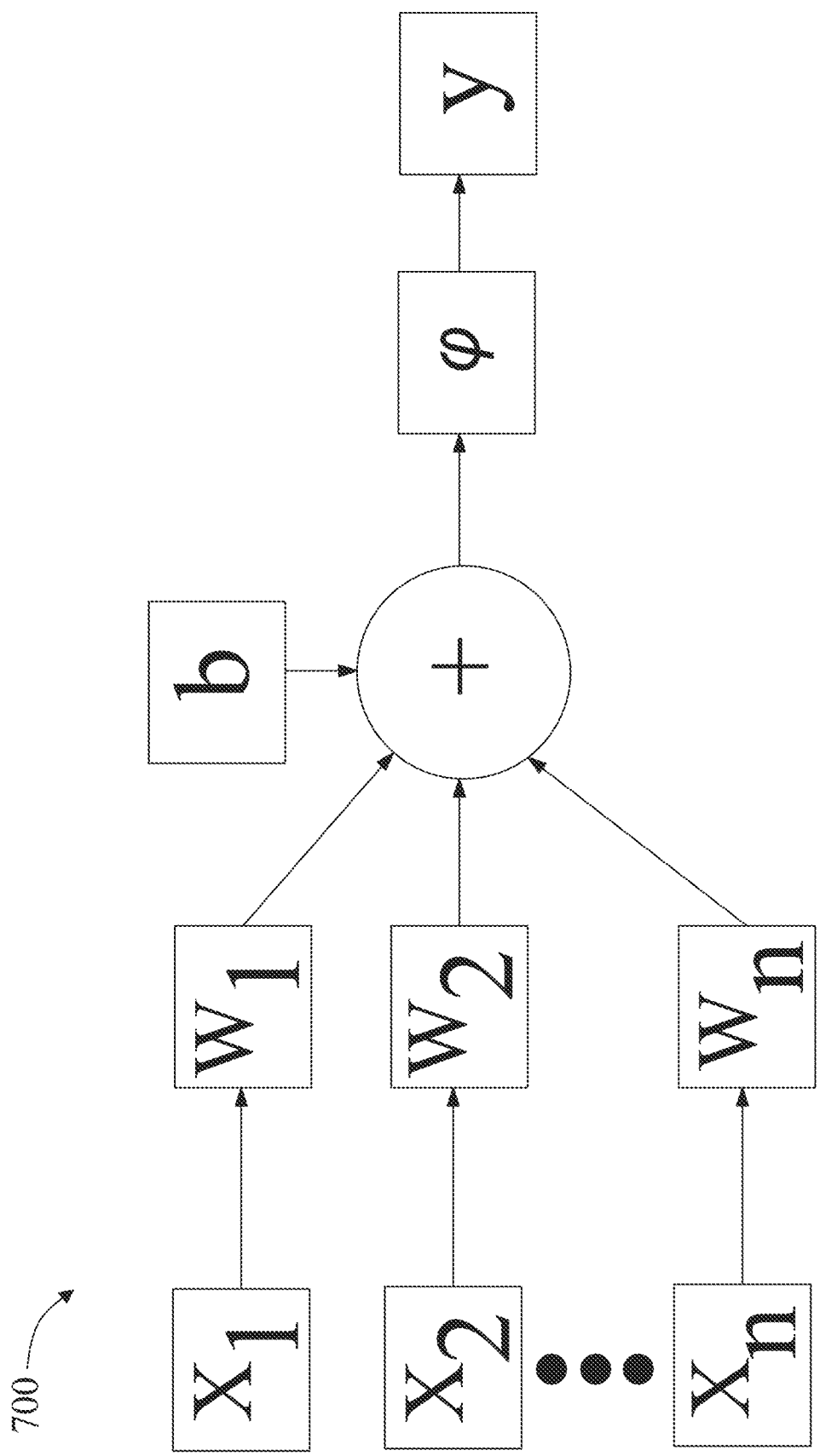
FIG. 7 is a diagram of an exemplary embodiment of a node of a neural network.

Referring now to FIG. 7, an exemplary embodiment of a node 700 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
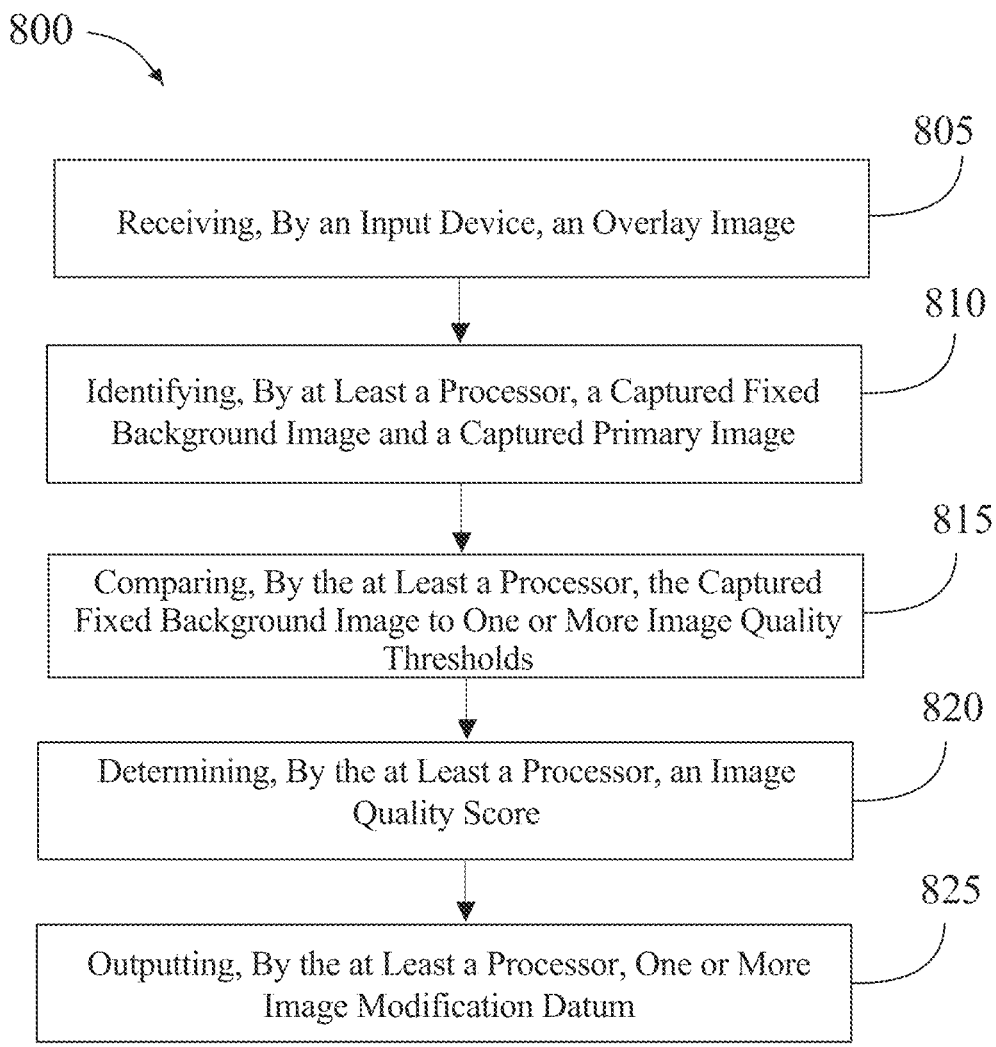
FIG. 8 is a flow diagram illustrating an exemplary embodiment of a method standardization of electrocardiogram signal images.

Referring now to FIG. 8, a method for standardization of electrocardiogram signal images is described. At step 805, method 800 includes receiving, by an imaging device, an overlay image. In one or more embodiments, imaging device may be included an in input device. In one or more embodiments, receiving, by the imaging device, the overlay image includes securing, using a transparent panel, a primary image atop a fixed background image, illuminating, using a light source, the primary image and the fixed background image and capturing, using the imaging device, the fixed background image and the primary image wherein the imaging device is positioned proximal to the transparent panel. This may be implemented with reference to FIGS. 1-8 and without limitation.

With continued reference to FIG. 8, at step 810, method 800 includes identifying, by at least a processor, a captured fixed background image and a captured primary image within the overlay image, wherein the captured primary image includes a plurality of electrocardiogram signals. In on or more embodiments, the captured fixed background image includes a color gamut. In one or more embodiments, the captured fixed background image includes a reference electrocardiogram signal. This may be implemented with reference to FIGS. 1-8 and without limitation.

With continued reference to FIG. 8, at step 815 method 800 includes comparing, by the at least a processor, the captured fixed background image to one or more image quality thresholds. In one or more embodiments, comparing, by the at least a processor, the captured fixed background image to one or more image quality thresholds includes comparing the captured fixed background image to a fixed reference image. This may be implemented with reference to FIGS. 1-8 and without limitation.

With continued reference to FIG. 8, at step 820, method 800 includes determining, by the at least a processor, an image quality score of the primary image as a function of the captured fixed background image. This may be implemented with reference to FIGS. 1-8 and without limitation.

With continued reference to FIG. 8, at step 825 method 800 includes outputting, by the at least a processor, one or more image modification datum as a function of the image quality score. In one or more embodiments, outputting, by the at least a processor, the one or more image modification datum as a function of the image quality score includes generating one or more image modification parameters for the input device. In one or more embodiments, outputting, by the at least a processor, the one or more image modification datum as a function of the image quality score includes modifying at least one configurable setting on the input device. In one or more embodiments, outputting, by the at least a processor, the one or more image modification datum as a function of the image quality score includes training a modification machine learning model as a function of modification training data having a plurality of image quality scores correlated to a plurality of image modification datums, iteratively generating the one or more image modification datum as a function of the modification machine learning model and the modification training data, iteratively generating an updated overlay image as a function of the one or more image modification datum having an updated fixed background image and an updated primary image and iteratively determining an updated image quality score of the updated primary image as a function of the updated fixed background image. In one or more embodiments, outputting image modification datum includes generating an updated overlay image as a function of the overlay image and the image quality score. In one or more embodiments, method 800 includes determining, by the at least a processor, an updated image quality score of the captured primary image as a function of the output of the image modification datum. This may be implemented with reference to FIGS. 1-8 and without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
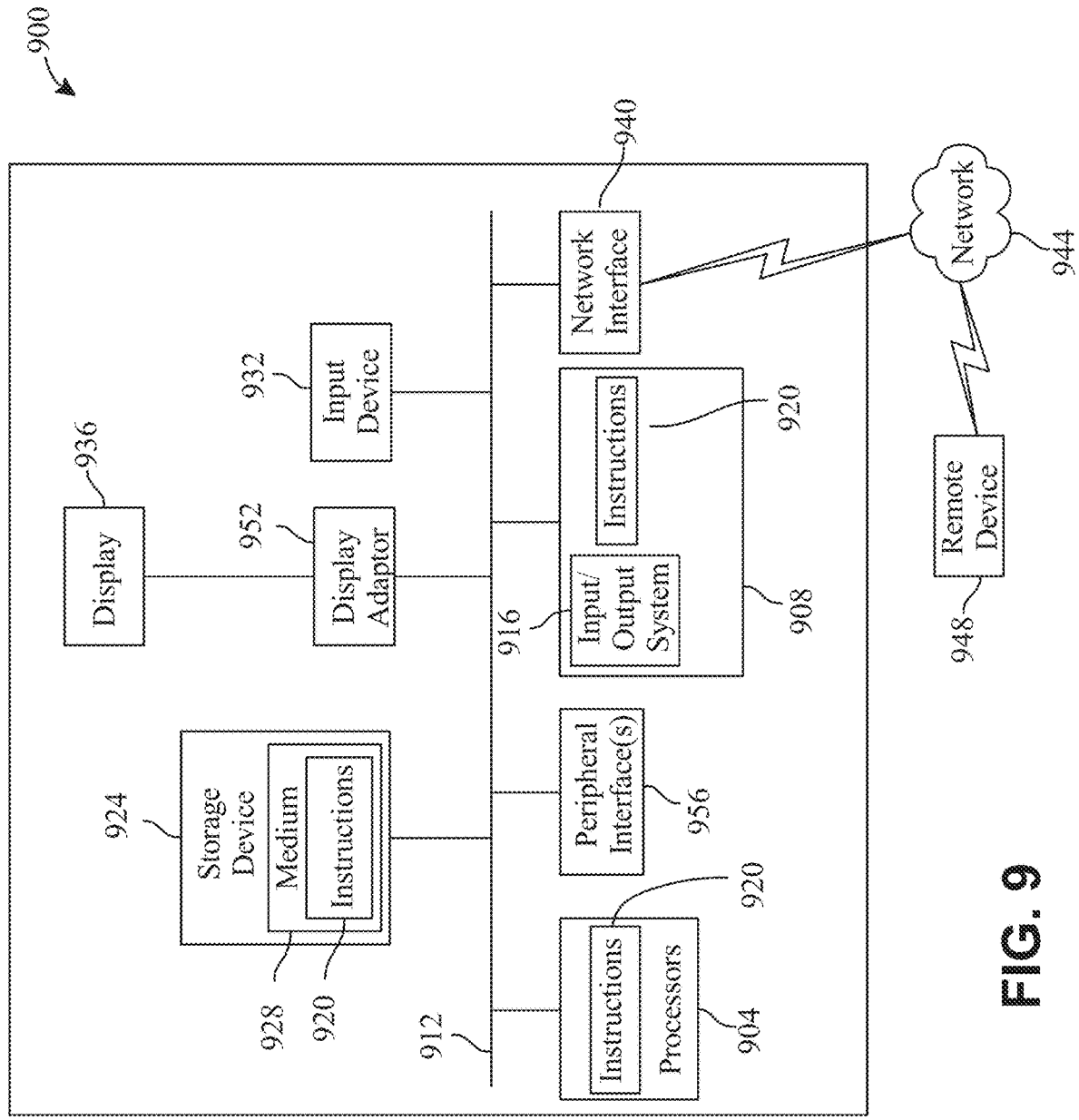
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, apparatuses and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for standardization of electrocardiogram signal images, the apparatus comprising:
   an imaging device;
   at least a processor; and
   a memory communicatively connected to the at least a processor, the memory containing instructions configuring the at least a processor to:
     receive an overlay image from the imaging device;
     identify a captured fixed background image and a captured primary image within the overlay image, wherein the captured primary image comprises a plurality of electrocardiogram signals;
     compare the captured fixed background image to one or more image quality thresholds;
     determine an image quality score of the captured primary image as a function of the comparison of the captured fixed background image to the one or more image quality thresholds; and
     output one or more image modification datum as a function of the image quality score.

2. The apparatus of claim 1, wherein outputting the one or more image modification datum as a function of the image quality score comprises generating an updated overlay image as a function of the overlay image and the image quality score.

3. The apparatus of claim 1, wherein the captured fixed background image comprises a color gamut.

4. The apparatus of claim 1, wherein the captured fixed background image comprises a reference electrocardiogram signal.

5. The apparatus of claim 1, wherein comparing the captured fixed background image to the one or more image quality thresholds comprises comparing the captured fixed background image to a fixed reference image.

6. The apparatus of claim 1, wherein outputting the one or more image modification datum as a function of the image quality score comprises generating one or more image modification parameters for the imaging device.

7. The apparatus of claim 1, further comprising iteratively determining an updated image quality score of the captured primary image as a function of the one or more image modification datum.

8. The apparatus of claim 1, further comprising an input device, the input device comprising:
a transparent panel configured to secure a primary image atop a fixed background image;
a light source configured to illuminate the primary image and the fixed background image; and
the imaging device positioned proximal to the transparent panel, wherein the imaging device is configured to capture the fixed background image and the primary image.

9. The apparatus of claim 8, wherein comparing the captured fixed background image to the one or more image quality thresholds comprises:
generating a two dimensional matrix of a position of one or more geometric patterns of the captured fixed background image; and
comparing the two dimensional matrix to one or more image quality thresholds.

10. The apparatus of claim 1, wherein outputting the one or more image modification datum as a function of the image quality score comprises:
training a modification machine learning model as a function of modification training data comprising a plurality of image quality scores correlated to a plurality of image modification datums;
iteratively generating the one or more image modification datum as a function of the modification machine learning model and the modification training data;
iteratively generating an updated overlay image as a function of the one or more image modification datum comprising an updated fixed background image and an updated primary image; and
iteratively determining an updated image quality score of the updated primary image as a function of the updated fixed background image.

11. A method for standardization of electrocardiogram signal images, the method comprising:
receiving, by an imaging device, an overlay image;
identifying, by at least a processor, a captured fixed background image and a captured primary image within the overlay image, wherein the captured primary image comprises a plurality of electrocardiogram signals;
comparing, by the at least a processor, the captured fixed background image to one or more image quality thresholds;
determining, by the at least a processor, an image quality score of the captured primary image as a function of the comparison of the captured fixed background image to the one or more image quality thresholds; and
outputting, by the at least a processor, one or more image modification datum as a function of the image quality score.

12. The method of claim 11, wherein outputting, by the at least a processor, the one or more image modification datum as a function of the image quality score comprises generating an updated overlay image as a function of the overlay image and the image quality score.

13. The method of claim 11, wherein the captured fixed background image comprises a color gamut.

14. The method of claim 11, wherein the captured fixed background image comprises a reference electrocardiogram signal.

15. The method of claim 11, wherein comparing, by the at least a processor, the captured fixed background image to the one or more image quality thresholds comprises comparing the captured fixed background image to a fixed reference image.

16. The method of claim 11, wherein outputting, by the at least a processor, the one or more image modification datum as a function of the image quality score comprises generating one or more image modification parameters for the imaging device.

17. The method of claim 11, further comprising determining, by the at least a processor, an updated image quality score of the captured primary image as a function of the one or more image modification datum.

18. The method of claim 11, wherein receiving, by the imaging device, the overlay image comprises:
securing, using a transparent panel, a primary image atop a fixed background image;
illuminating, using a light source, the primary image and the fixed background image; and
capturing, using the imaging device, the fixed background image and the primary image wherein the imaging device is positioned proximal to the transparent panel.

19. The method of claim 18, wherein comparing, by the at least a processor, the captured fixed background image to the one or more image quality thresholds comprises:
generating a two dimensional matrix of a position of one or more geometric patterns of the captured fixed background image; and
comparing the two dimensional matrix to one or more image quality thresholds.

20. The method of claim 11, wherein outputting, by the at least a processor, the one or more image modification datum as a function of the image quality score comprises:
training a modification machine learning model as a function of modification training data comprising a plurality of image quality scores correlated to a plurality of image modification datums;
iteratively generating the one or more image modification datum as a function of the modification machine learning model and the modification training data;
iteratively generating an updated overlay image as a function of the one or more image modification datum comprising an updated fixed background image and an updated primary image; and
iteratively determining an updated image quality score of the updated primary image as a function of the updated fixed background image.

* * * * *